United States Patent

Jeong et al.

(10) Patent No.: US 7,199,127 B2
(45) Date of Patent: Apr. 3, 2007

(54) PURINE NUCLEOSIDES

(75) Inventors: Lak Shin Jeong, Seoul (KR); Kenneth A. Jacobson, Silver Spring, MD (US); Hyung Ryong Moon, Seoul (KR); Hea Ok Kim, Seoul (KR)

(73) Assignees: United States of America, Represented by the Secretary, Department of Health and Human Services, Washington, DC (US); Ewha Womans University, Seoul (KR)

( * ) Notice: Subject to any disclaimer, the term of this patent is extended or adjusted under 35 U.S.C. 154(b) by 0 days.

(21) Appl. No.: 10/530,552

(22) PCT Filed: Oct. 24, 2003

(86) PCT No.: PCT/US03/33987

§ 371 (c)(1),
(2), (4) Date: May 17, 2005

(87) PCT Pub. No.: WO2004/038006

PCT Pub. Date: May 6, 2004

(65) Prior Publication Data

US 2005/0256143 A1    Nov. 17, 2005

Related U.S. Application Data

(60) Provisional application No. 60/482,459, filed on Jun. 26, 2003.

(30) Foreign Application Priority Data

Oct. 25, 2002    (KR) .............. 10-2002-0065441

(51) Int. Cl.
*C07D 473/40*    (2006.01)
*C07D 495/04*    (2006.01)
*C07D 407/06*    (2006.01)
*A61K 31/52*    (2006.01)
*A61P 35/00*    (2006.01)

(52) U.S. Cl. ............... 514/263.23; 536/27.62; 536/27.63; 536/27.7; 536/27.6; 536/27.22; 514/45; 514/46; 544/276; 544/277; 549/50; 549/435; 549/448

(58) Field of Classification Search ........... 536/27.62, 536/27.63, 27.7, 27.6, 27.22; 544/276, 277; 514/45, 46, 263.23
See application file for complete search history.

(56) References Cited

U.S. PATENT DOCUMENTS 5,620,676 A   4/1997   Jacobson et al.
5,688,774 A   11/1997  Jacobson et al.

OTHER PUBLICATIONS

Bloch, et al., *J. Med. Chem.*; 1967; 10(5) pp. 908-912.*
Boullais et al., *Tetrahedron*, vol. 39, pp. 759-765, (1983).
Jeong et al., *Tet. Lett.*, vol. 37, pp. 2353-2356, (1996).
Jacobson et al., *J. Med. Chem*, vol. 38, pp. 1720-1735, (1995).
Jacobson et al., *Purinergic Approaches in Experimental Therapeutics*, Chap. 6, pp. 101-128, (1997).
Jacobson et al., *J. Med. Chem*, 35, pp. 407-422, (1992).
McCormick et al., *Proc. R. Acad. Sciences*, vol. 83B, pp. 125-138 (1983).
McCormick et al., *JCS, Perkins I*, pp. 500-505, (1978).

* cited by examiner

*Primary Examiner*—Mark L. Berch
(74) *Attorney, Agent, or Firm*—Leydig, Voit & Mayer, Ltd.

(57) ABSTRACT

Disclosed are purine nucleoside compounds that are selective to $A_3$ adenosine receptors and are useful for the treatment of cancer and inflammatory diseases. The compounds are shown by the following general formula (I), including isomers thereof:

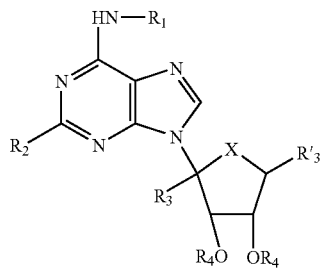

(I)

wherein X is sulfur or oxygen; $R_1$ is hydrogen, alkyl, benzyl, halobenzyl, or phenylalkyl; $R_2$ is hydrogen, halogen, alkoxy, alkenyl, alkynyl, alkylthio, or thio; $R_3$ and $R_3'$ are hydrogen, hydroxyalkyl, alkoxycarbonyl, or alkylaminocarbonyl, whereas $R_3$ and $R_3'$ do not have identical substituents simultaneously; and $R_4$ is hydrogen or alkyl. Also disclosed are a pharmaceutical composition comprising a compound of formula (I), an isomer, or its pharmacologically acceptable salt as an active ingredient and a method for preventing or treating various diseases, state, or condition, including asthma, inflammation, cerebral ischemia, heart diseases, and cancer.

11 Claims, 3 Drawing Sheets

PURINE NUCLEOSIDES

CROSS-REFERENCE TO RELATED PATENT APPLICATIONS

This patent application claims the benefit of Korean Patent Application No. 2002-0065441, filed Oct. 25, 2002, and U.S. Provisional Patent Application No. 60/482,459, filed Jun. 26, 2003, the disclosures of which are incorporated by reference.

FIELD OF THE INVENTION

This invention pertains to purine nucleosides in general, and in particular to purine thionucleosides, pharmaceutical compositions containing one or more such nucleosides, and a method of treatment of an animal using such nucleosides. These nucleosides are selective to $A_3$ adenosine receptors as agonists or antagonists.

BACKGROUND OF THE INVENTION

Adenosine is a compound that executes various physiological functions through specific receptors in cell membranes. Extracellular adenosine acts as a neurotransmitter in a variety of physiological systems. In general, adenosine counterbalances excessive activities of a given organ and thereby provides protection from the harmful effect of stress (Jacobson, K. A. et al.; *J. Med. Chem.*, 35, pp. 407–422, 1992). This is a partially formed negative feedback loop in an attempt to decrease the cellular energy demand by adenosine formed via decomposition of endocellular and extracellular ATP (adenosine triphosphate) and to increase oxygen supply. Adenosine is important in maintaining the normality of essential organs such as the brain, heart and kidney. For example, it was proved that the injection of an adenosine agonist into the brain has a neuroprotective effect, and it is also known to be related to pain, intelligence, movement, and sleep.

Adenosine receptors have been classified as P1 and P2 receptors through pharmacological study and molecular cloning. Adenosine acts as a substrate for P1 receptors whereas ATP, ADP, UTP, and UDP act as substrates for P2 receptors to manifest physiological activity. Among these, four different subtypes of adenosine receptors were identified for P1 receptors, which were classified as $A_1$, $A_2$, or $A_3$ based on the ligand affinity, distribution in the system, and functional process. $A_2$ is again divided into $A_{2a}$ and $A_{2b}$. These adenosine receptors form one class of G-protein-coupled receptors. The adenosine $A_1$, $A_{2a}$ and $A_{2b}$ receptors were pharmacologically identified using various selective ligands. However, the adenosine $A_3$ receptor was first identified in 1992 (Zhou, Q. Y. et al.; *Proc. Natl. Acad. Sci. USA*, 89, pp. 7432–7436, 1992). Numerous studies are being carried out to identify the particular physiological function of this receptor.

Adenosine $A_1$ and $A_2$ receptor agonists are usually antihypertensives, antipsychotic, anti-arrhythmia drugs, and fat metabolism inhibitors (diabetes treatment drugs), and neuroprotective drugs, which have been studied quite well. Antagonists are xanthine derivatives or compounds wherein various heterocycles are fused together, which have been developed for anti-asthmatics, antidepressants, anti-arrhythmia drugs, renal protection drugs, anti-Parkinson's drugs, and nootropics. However, recently commercialized drugs are adenosine itself for treatment of supraventricular tachycardia, and the adenosine transfer inhibiting drug, dipyridamole, which is being used as a supplemental drug for warfarin in preventing blood coagulation after heart surgery. Such development has been unsuccessful because adenosine receptors are present all over the system, and there are various concomitant pharmacological effects until the receptor is activated, and therefore no compound can activate only the adenosine receptor.

Among the adenosine receptors, the $A_3$ adenosine receptor has recently been identified as unlike the widely known $A_1$ and $A_2$ adenosine receptors, and therefore its role has not yet been elucidated. Various studies are in progress for development of selective ligands for the $A_3$ adenosine receptor. For pharmacological study on the adenosine $A_3$ receptor, three radiolabeled ligands such as [$^{125}$I]ABA (N$^6$-(4-amino-3-$^{125}$I [iodo]benzyl)adenosine), [$^{125}$I]APNEA ([$^{125}$I]N6-2-(4-aminophenyl)ethyl adenosine) or [$^{125}$I]AB-MECA ([$^{125}$I] 4-aminobenzyl-5'-N-methylcarboxyamidoadenosine) are being employed. When $A_3$ adenosine receptor was expressed in Chinese hamster ovary (CHO) cells, it had an inhibiting effect on adenylyl cyclase, the enzyme that produces cAMP from ATP. When the $A_3$ adenosine receptor was activated by an agonist, it was proved that phosphatidyl inositol decomposed to activate GTP-dependent phospholipase C (guanosine triphosphate-dependent phospholipase), the enzyme that produces inositol phosphate and DAG (Ramkumar, V., et al.; *J. Biol. Chem.*, 268, pp. 168871–168890, 1993: Abbracchio, M. P. et al.; *Mol. Pharmacol.*, 48, pp. 1038–1045, 1995). This discovery explains the potential response pathway by $A_3$ adenosine receptor activation for cerebral ischemia because this secondary transmitter system means the response pathway of nerve damage in brain ischemia. In addition, the adenosine $A_3$ agonist has a protective effect against brain diseases like epilepsy, and a protective effect for the heart. Activation of the $A_3$ adenosine receptor results in the emission of inflammation-inducing factor like histamine from mast cells, and contracts organs. High concentrations of agonist or antagonist may result in apoptosis in immune cells. An agonist of $A_3$ adenosine receptors inhibits the generation of tumor necrosis factor (TNF-α), which is the inflammation transmitter, and also inhibits the formation of MIP-1α, interleukin-12, and interferon-γ, which are inflammation mediators. Therefore, $A_3$ adenosine antagonists have the potential for development as anti-inflammatories and antiasthmatics. The foregoing shows that there exists need for highly $A_3$ selective adenosine receptor agonists.

Among the compounds that have been developed and studied so far, N$^6$-(3-iodobenzyl)-5'-(N-methylcarbamoyl) adenosine (IB-MECA) which is shown in the following Structure 1, and N$^6$-(3-iodobenzyl)-2-chloro-5'-(N-methylcarbamoyl)adenosine (Cl-IB-MECA) shown in Structure 2 are representative selective adenosine $A_3$ ligands which showed high selectivity for $A_3$ adenosine receptors over $A_1$ and $A_2$ adenosine receptors.

[Structure 1]

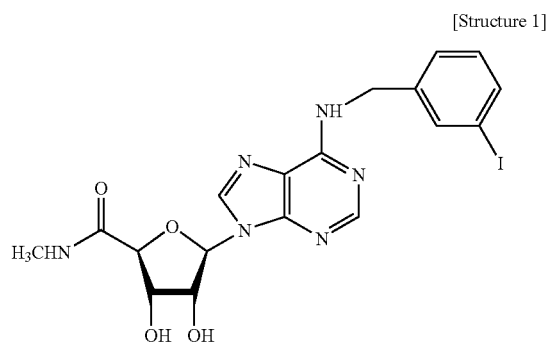

-continued

[Structure 2]

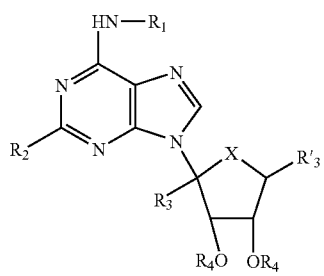

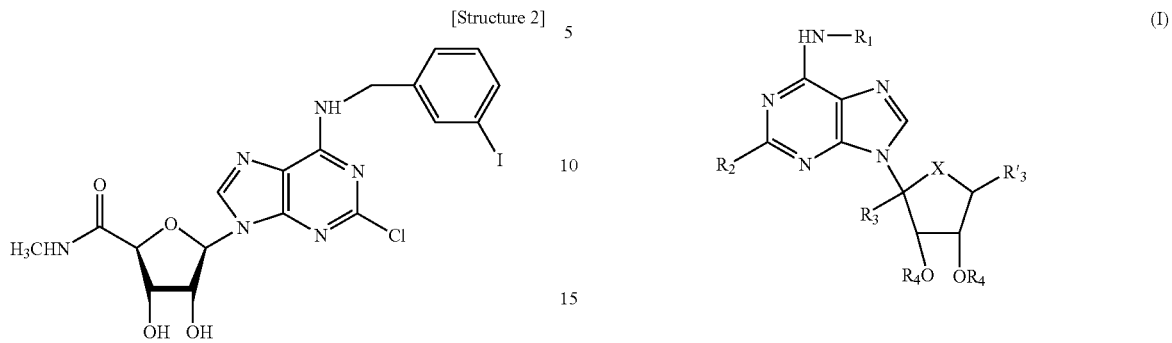

The invention provides highly selective $A_3$ adenosine receptor agonists and antagonists. These and other advantages of the invention, as well as additional inventive features, will be apparent from the description of the invention provided herein.

BRIEF SUMMARY OF THE INVENTION

The present invention provides purine nucleoside compounds which are selective to $A_3$ adenosine receptors and are useful for the treatment of cancer and inflammatory diseases. The present invention provides compounds shown by the following general formula (I):

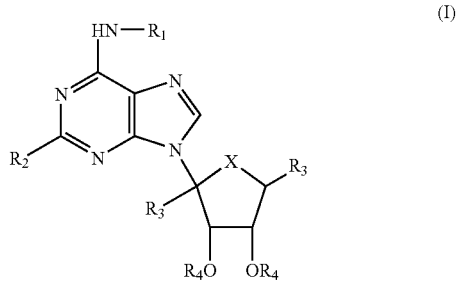

and isomers thereof, wherein X is sulfur or oxygen; $R_1$ is hydrogen, alkyl, benzyl, halobenzyl, or phenylalkyl; $R_2$ is hydrogen, halogen, alkoxy, alkenyl, alkynyl, alkylthio, or thio; $R_3$ and $R_3'$ are hydrogen, hydroxyalkyl, alkoxycarbonyl, or alkylaminocarbonyl, whereas $R_3$ and $R_3'$ do not have identical substituents simultaneously; and $R_4$ is hydrogen or alkyl.

The foregoing need has been fulfilled to a great extent by the present invention that provides purine nucleosides selective to $A_3$ adenosine receptors. Thus, in an embodiment, the present invention provides a compound of formula (I):

wherein X is sulfur or oxygen; $R_1$ is hydrogen, $C_1$–$C_5$ alkyl, benzyl, halobenzyl, or phenyl $C_1$–$C_5$ alkyl; $R_2$ is hydrogen, halogen, $C_1$–$C_5$ alkoxy group, $C_2$–$C_6$ alkenyl, $C_2$–$C_6$ alkynyl, $C_1$–$C_5$ alkylthio, or thio; $R_3$ and $R_3'$ may be the same or different and are hydrogen, hydroxy $C_1$–$C_5$ alkyl, $C_1$–$C_5$ alkoxycarbonyl, or $C_1$–$C_5$ alkylaminocarbonyl; $R_4$ is hydrogen or $C_1$–$C_5$ alkyl; or a pharmaceutically acceptable salt, or isomer thereof. In an embodiment, $R_3$ and $R_3'$ are not the same. In a preferred embodiment, X is sulfur.

DETAILED DESCRIPTION OF THE INVENTION

Figure 1:
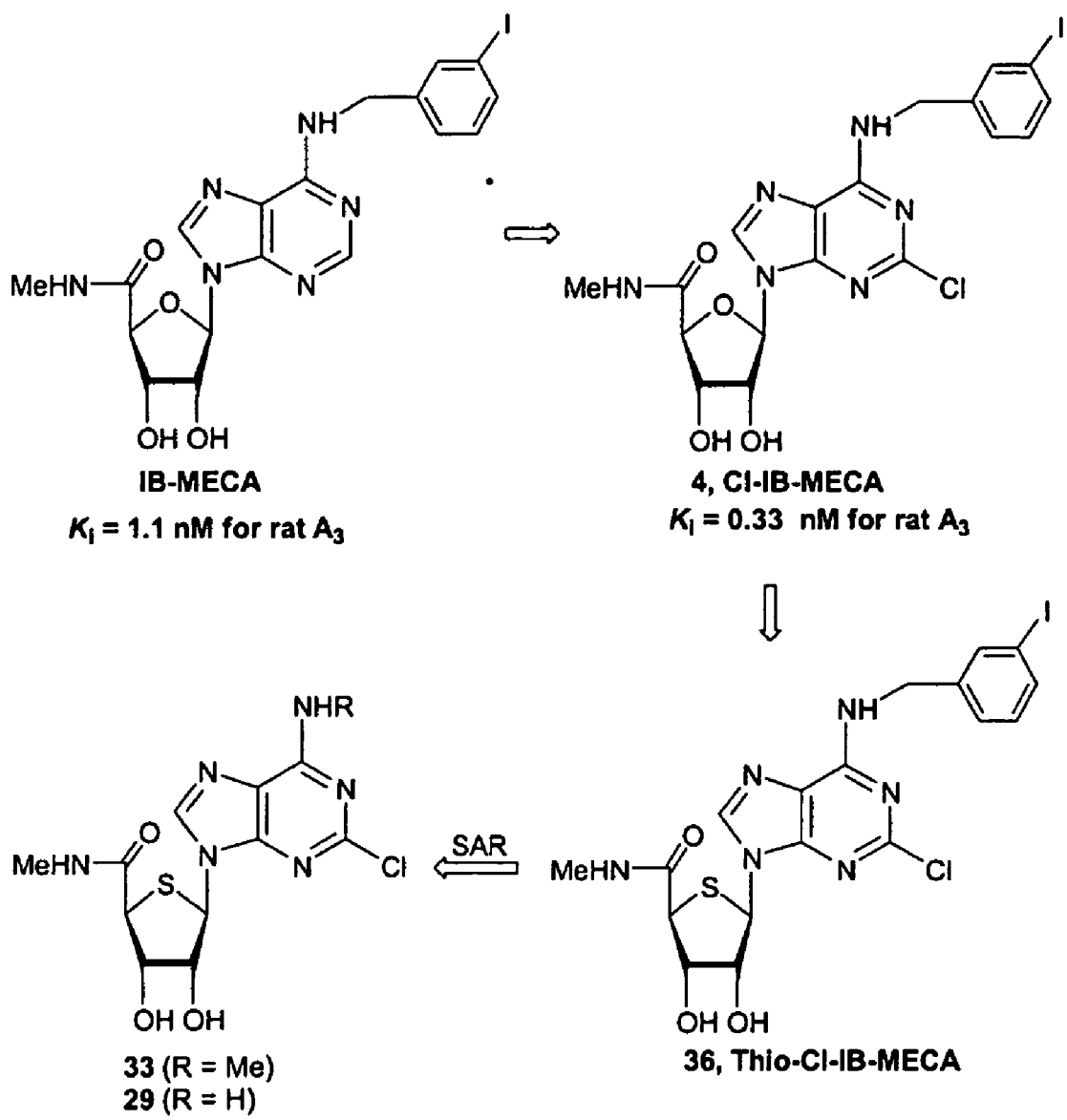
FIG. 1 depicts the formulas of IB-MECA and Cl-EB-MECA and compounds 29, 33, and 36 of the present invention

The foregoing need has been fulfilled to a great extent by the present invention that provides purine nucleosides selective to $A_3$ adenosine receptors. Thus, in an embodiment, the present invention provides a compound of formula (I):

wherein X is sulfur or oxygen; $R_1$ is hydrogen, $C_1$–$C_5$ alkyl, benzyl, halobenzyl, or phenyl $C_1$–$C_5$ alkyl; $R_2$ is hydrogen, halogen, $C_1$–$C_5$ alkoxy group, $C_2$–$C_6$ alkenyl, $C_2$–$C_6$ alkynyl, $C_1$–$C_5$ alkylthio, or thio; $R_3$ and $R_3'$ may be the same or different and are hydrogen, hydroxy $C_1$–$C_5$ alkyl, $C_1$–$C_5$ alkoxycarbonyl, or $C_1$–$C_5$ alkylaminocarbonyl; $R_4$ is hydrogen or $C_1$–$C_5$ alkyl; or a pharmaceutically acceptable salt, or isomer thereof. In an embodiment, $R_3$ and $R_3'$ are not the same. In a preferred embodiment, X is sulfur.

In embodiments of the compounds of general formula (I), $R_1$ is 3-iodobenzyl, $R_2$ is chloride, $R_3$ is methylaminocarbonyl, $R_3'$ and $R_4$ are hydrogen, and X is sulfur, includes the compounds of the following general formula (II) and its isomers.

In a specific embodiment, the present invention provides compounds of formula (II) or an isomer thereof:

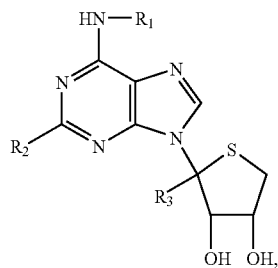

(II)

wherein $R_1$, $R_2$ and $R_3$ are as defined above for formula (I). A preferred compound of formula (II) is (2R,3S,4R)-2-[2-chloro-6-(3-iodobenzylamino)purin-9-yl]-3,4-dihydroxytetrahydrothiophene-2-carboxylic acid methyl amide.

The compounds of the aforementioned general formula (I), includes the compound of the following general formula (III) and its isomers. In accordance with another embodiment, the present invention provides compounds of the formula (III) or isomers thereof:

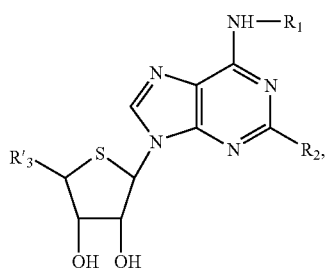

(III)

wherein $R_1$, $R_2$ and $R'_3$ are as defined for formula (I), and specifically, $R_1$ is hydrogen, methyl group, or 3-iodobenzyl group, $R_2$ is chloride, $R_3$ and $R_4$ are hydrogen, $R_3'$ is methylaminocarbonyl group or hydroxymethyl group, and X is sulfur.

Specific examples of such compounds are (2R,3R,4S,5R)-2-[2-chloro-6-(3iodobenzylamino)purin-9-yl]-5-hydroxymethyltetrahydrothiophene-3,4-diol, (2R,3R,4S,5R) -2-(2-chloro-6-methylaminopurin-9-yl]-5hydroxymethyl-tetrahydrothiophene-3,4-diol, (2R,3R,4S,5R)-2-(2chloro-6-aminopurin-9-yl]-5-hydroxymethyltetrahydrothiophene-3, 4-diol, (2S,3S,4R,5R)-5-(6-amino-2-chloro-purin-9-yl]-3,4-dihydroxytetrahydrothiophene-2-carboxylic acid methyl amide, (2S,3S,4R,5R)-5-(2-chloro-6-methylaminopurin-9-yl]-3,4-dihydroxytetrahydrothiophene-2-carboxylic acid methyl amide, and (2S,3S,4R,5R)-5-[2-chloro-6-(3-iodobenzylamino)purin-9-yl]-3,4-dihydroxytetrahydrothiophene-2-carboxylic acid methyl amide.

In a further embodiment, the present invention provides compounds of the general formula (IV) or isomers thereof:

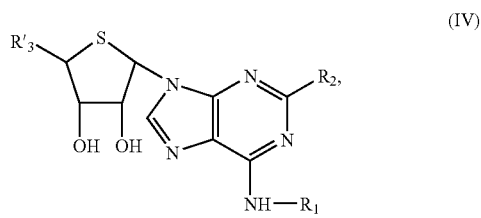

(IV)

wherein $R_1$, $R_2$ and $R'_3$ are as defined above for formula (I). A specific example of such compounds is (2S,3R,4S,5R)-2-[2-chloro-6-(3-iodobenzylamino)purin-9-yl]-5-hydroxymethyltetrahydrothiophene-3,4-diol.

The present invention further provides a manufacturing method for compounds with the aforementioned general formula (I), which can be chemically synthesized by the method as illustrated in the following Reaction Equations 1–7. However, the synthetic method is not limited to these examples. The following Reaction Equations list each step of the manufacturing method of the representative compounds of the present invention.

[Reaction equation 1]

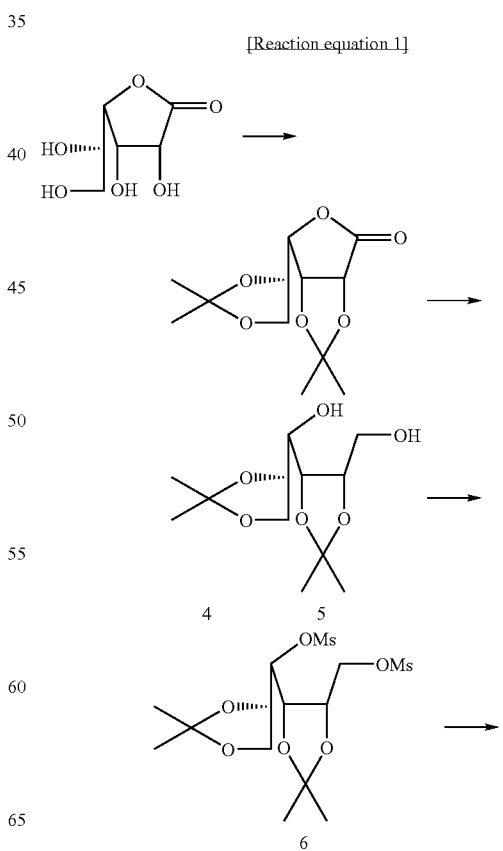

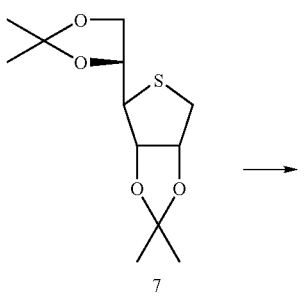

7

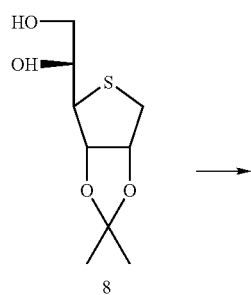

8

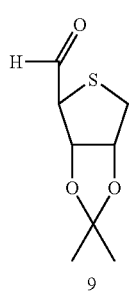

9

As shown in Reaction Equation 1, the compound with chemical formula 4 can be synthesized from D-gulonic γ-lactone by reacting with dry acetone as a reagent and solvent at the same time using concentrated sulfuric acid as an acid catalysis in the presence of anhydrous copper (II) sulfate. This reaction can employ an inorganic acid such as hydrochloric acid or an organic acid such as p-toluenesulfonic acid as an acid catalyst instead of the concentrated sulfuric acid. As a dehydrating agent, it is possible to use a molecular sieve or anhydrous magnesium sulfate in addition to anhydrous copper(II) sulfate. The synthesized compound 4 was reacted with lithiumaluminum hydride to obtain compound 5. It is preferable to use an inert solvent such as ethyl ether, petroleum ether, dichloromethane, or tetrahydrofuran. It is also possible to use a metal hydride such as sodium borohydride instead of lithiumaluminum hydride. Compound 5 synthesized herein was reacted with methanesulfonyl chloride to obtain compound 6. It is preferable to use an amine reagent such as pyridine or triethylamine as a solvent and reagent at the same time, or in a mixture with an inert solvent such as ethyl ether, petroleum ether, dichloromethane, tetrahydrofuran, or N,N-dimethylformamide. As a reaction catalyst, N,N-dimethylaminopyridine or 2,6-lutidine may be used. A compound with the aforementioned chemical formula 7 can be obtained by reacting compound 6 with sodium sulfide, and it is also possible to use a sodium alkoxide after substitution reaction with a thioester like metal thioacetate, instead of sodium sulfide. It is preferred to use N,N-dimethylformamide and dimethyl sulfoxide as a solvent. It is also possible to react in a low-molecular-weight alcohol such as methanol or ethanol, which may be mixed with water or an inert organic solvent. Compound 7 synthesized herein was reacted with an aqueous acetic acid solution to obtain compound 8. Instead of acetic acid, an inorganic acid such as sulfuric acid or hydrochloric acid or an organic acid such as p-toluenesulfonic acid can be used with water or a low-molecular-weigh alcohol like methanol alone as a solvent or as a mixture with an organic solvent. Compound 9 with aforementioned chemical formula 9 can be obtained by reacting compound 8 with lead tetraacetate, wherein it is possible to use sodium metaperiodate at a low temperature instead of lead tetraacetate. It is preferred to use an inert solvent such as ethyl acetate, ethyl ether, petroleum ether, dichloromethane, tetrahydrofuran, or N,N-dimethylformamide.

[Reaction equation 2]

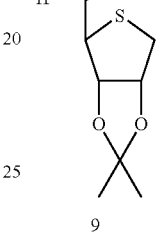 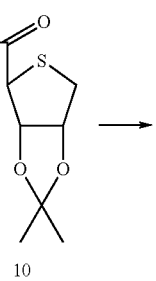

9         10

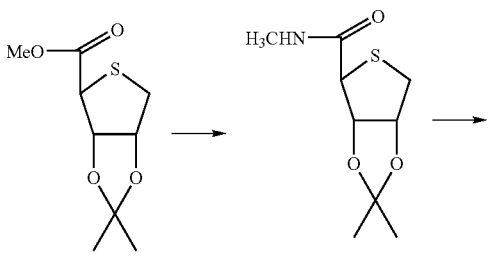

11         12

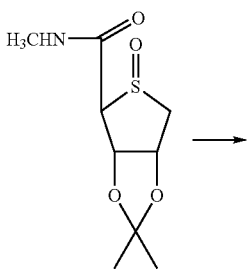

13

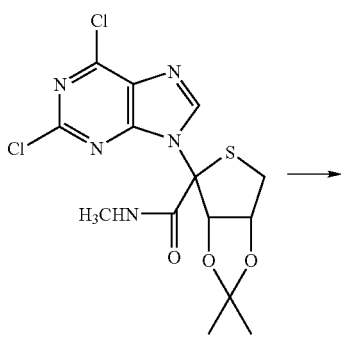

14

-continued

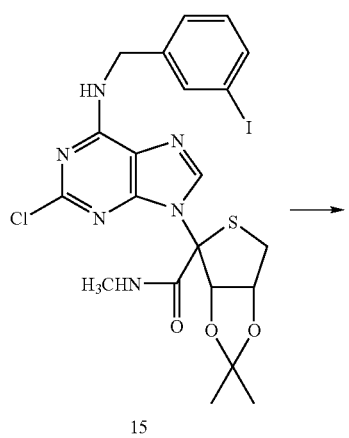

15

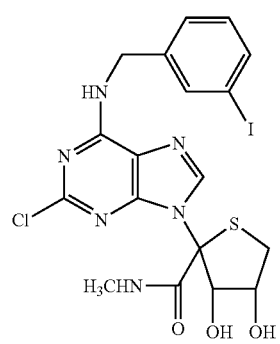

16

As shown in Reaction Equation 2, the compound with the aforementioned chemical formula 10 can be obtained by reacting compound 9 from reaction equation 1 with pyridinium dichromate in N,N-dimethylformamide solvent. The compound of chemical formula 11 can be obtained by reacting the compound of chemical formula 10 with dimethyl sulfate in the presence of potassium carbonate, wherein it is possible that dimethyl sulfate can be replaced with a methyl halide such as methyl iodide or diazomethane, and potassium carbonate can be replaced with an inorganic base such as sodium carbonate or an organic base such as DBU or n-butyllithium. It is also possible to use acetone as a solvent, or an organic solvent such as tetrahydrofuran or dioxane.

The compound with chemical formula 12 can be obtained by the reaction of the compound with chemical formula 11 with methylaminetetrahydrofuran solution or aqueous solution. As a solvent, tetrahydrofuran alone can be used or water can be mixed with an inert solvent such as ethyl ether, petroleum ether, dichloromethane, tetrahydrofuran, or N,N-dimethylformamide. The compound of chemical formula 13 can be obtained by the reaction of the compound of chemical formula 12 with m-chloroperbenzoic acid, wherein it is possible to use sodium metaperiodate, t-butylperoxide, peracetic acid, or hydrogen peroxide instead of m-chloroperbenzoic acid. As a solvent, it is preferred that an inert solvent such as ethyl ether, petroleum ether, dichloromethane, tetrahydrofuran, N,N-dimethylformamide be used alone, or a mixed solvent of these inert solvents and water may be used.

The compound with chemical formula 14 can be obtained by reacting a compound having chemical formula 13 with silylated 2,6-dichloropurine in the presence of trimethylsilyl trifluoromethanesulfonate, wherein an inert solvent such as dichloroethane, chloroform, acetonitrile, or dichloromethane is preferred as a solvent. Silylated 2,6-dichloropurine can be prepared by the reaction of hexamethyldisilazane with 2,6-dichloropurine as a reagent and solvent in the presence of ammonium sulfate catalyst, or by the direct reaction of 2,6-dichloropurine with N,O-bis(trimethylsilyl)acetamide. The compound having chemical formula 15 was obtained by reacting the compound having chemical formula 14 with 3-iodobenzylamine hydrochloride in the presence of triethylamine base. Instead of triethylamine, an organic base such as pyridine, N,N-dimethylaminopyridine or 2,6-lutidine can be used. It is preferred to use a low-molecular-weigh alcohol like methanol or ethanol, 1,4-dioxane, tetrahydrofuran, or chloroform as a solvent. The compound having chemical formula 16 was prepared by reacting the compound having chemical formula 15 with an aqueous solution of acetic acid, wherein an inorganic acid such as sulfuric acid or hydrochloric acid or an organic acid such as p-toluenesulfonic acid may be substituted for the acetic acid, which can be mixed with water alone or a low-molecular-weight alcohol alone such as methanol as a solvent, or with a mixed solvent of water or low-molecular-weight alcohol and organic solvent.

[Reaction equation 3]

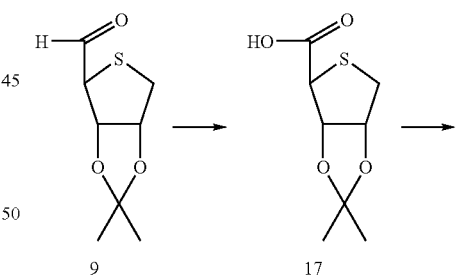

9                    17

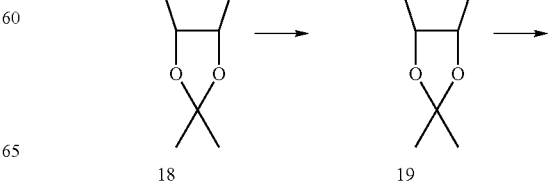

18                   19

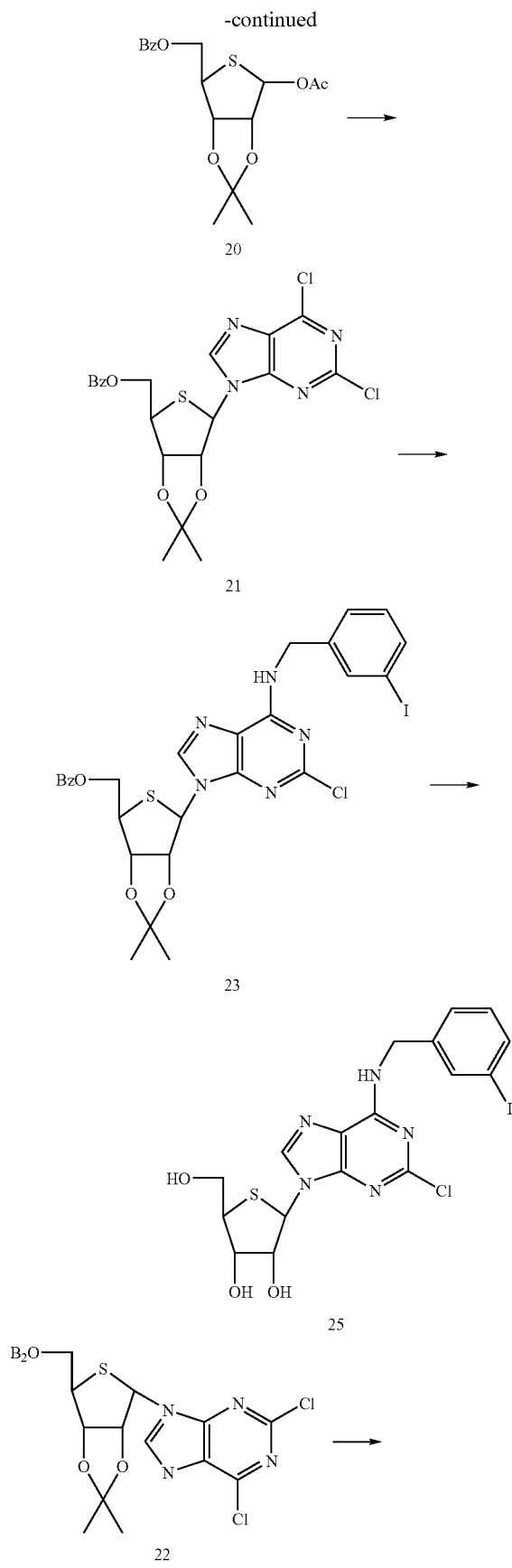

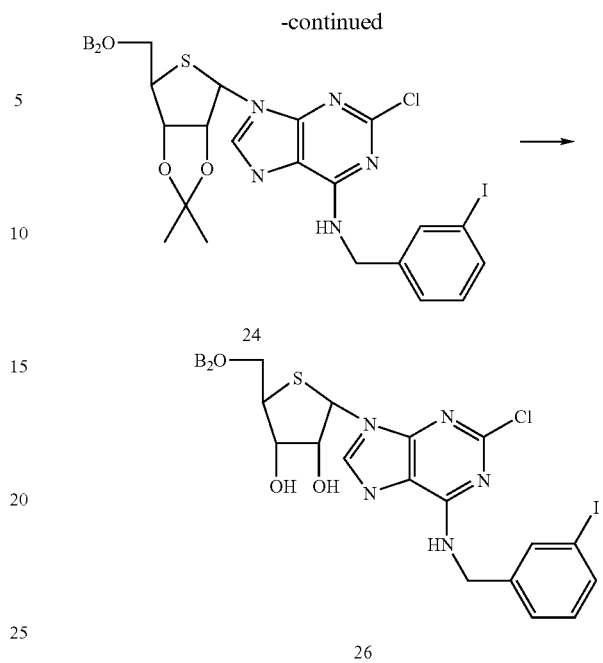

As shown in Reaction Equation 3, the compound having chemical formula 17 can be obtained by reacting the compound having chemical formula 9 with sodium borohydride, wherein it is preferred to use a low-molecular-weight alcohol such as methanol or ethanol, and it is also possible to carry out the reaction in a mixed solvent of these low-molecular-weight alcohols and dichloromethane, tetrahydrofuran, or chloroform. The compound having chemical formula 18 can be obtained by reacting the compound having chemical formula 17 with benzoyl chloride, wherein it is preferred to use an amine reagent like pyridine or triethylamine as both a solvent and reagent or by mixing with an inert solvent such as ethyl ether, petroleum ether, dichloromethane, tetrahydrofuran, N,N-dimethylformamide, or chloroform. As a reaction catalyst, N,N-dimethylaminopyridine or 2,6-lutidine may be used.

The compound having chemical formula 19 can be obtained by reacting the compound having chemical formula 18 and m-chlorobenzoic acid. Instead of m-chlorobenzoic acid, sodium metaperiodate, t-butylperoxide, peracetic acid, or hydrogen peroxide may be used. It is preferred to use an inert solvent alone such as ethyl ether, petroleum ether, dichloromethane, tetrahydrofuran, N,N-dimethylformamide, or to use a mixed solvent of an inert solvent and water. The compound having chemical formula 20 was obtained by reacting the compound having chemical formula 19 with acetic anhydride, wherein the acetic anhydride is preferred to be used as both a solvent and a reagent. In addition, it is desirable to increase the reactivity by adding an acetate ion such as sodium acetate or tetrabutylammonium acetate.

Each of the compounds having chemical formulas 21 and 22 can be obtained by reacting the compound having chemical formula 20 with silylated 2,6-dichloropurine in the presence of trimethylsilyl trifluoromethanesulfonate. As a solvent, it is preferred to use an inert solvent such as dichloroethane, chloroform, acetonitrile, or dichloromethane. The silylated 2,6-dichloropurine can be obtained by reacting 2,6-dichloropurine with hexamethyldisilazane used as both a solvent and a reagent in the presence of ammonium sulfate catalyst, or by direct reaction of 2,6-dichloropurine with N,O-bis(trimethylsilyl)acetamide. Instead of trimethylsilyl trifluoromethanesulfonate, an inorganic catalyst such as tin(IV) chloride may be used.

The compound having chemical formula 23 can be obtained by reacting the compound having chemical formula 21 with 3-iodobenzylamine hydrochloride in the presence of triethylamine base, wherein triethylamine can be replaced with an organic base such as pyridine, N,N-dimethylaminopyridine or 2,6-lutidine. As a solvent, it is preferred to use 1,4-dioxane, tetrahydrofuran, chloroform, or a low-molecular-weight alcohol such as methanol or ethanol. The compound having chemical formula 24 can be prepared by reacting the compound having chemical formula 22 with 3-iodobenzylamine hydrochloride in the presence of triethylamine base. Instead of triethylamine, an organic base such as pyridine, N,N-dimethylaminopyridine, or 2,6-lutidine may be used. As a solvent, 1,4-dioxane, tetrahydrofuran, chloroform, or a low-molecular-weight alcohol such as methanol or ethanol is preferred.

The compound having chemical formula 25 can be obtained by treating the resulting compound prepared in the following method with an aqueous acetic acid solution: by reacting the compound having chemical formula 23 with a metal alkoxide such as sodium methoxide or sodium ethoxide in a low-molecular-weight alcohol such as methanol or ethanol; by reacting the compound having chemical formula 23 with ammonia in an alcohol solvent such as methanol or ethanol; or by reacting the compound having chemical formula 23 with an inorganic base such as sodium carbonate or sodium hydrogen carbonate in a mixed solvent of water and a low-molecular-weight alcohol. The acetic acid may be substituted with an inorganic acid such as sulfuric acid or hydrochloric acid or an organic acid such as p-toluenesulfonic acid. As a solvent, it is also possible to use water alone or a low-molecular-weight alcohol like methanol alone or a mixed solvent with an organic solvent.

The compound having chemical formula 26 can be obtained by reacting an aqueous solution of acetic acid with the compounds resulting from the following methods: by reacting the compound having chemical formula 24 with a metal alkoxide such as sodium methoxide or sodium ethoxide in a low-molecular-weight alcohol solvent such as methanol or ethanol or in a mixed solvent with an inert solvent like dichloromethane or chloroform; by reacting the compound having chemical formula 24 with ammonia in an alcohol solvent such as methanol or ethanol; or by reacting the compound having chemical formula 24 with an inorganic base such as sodium carbonate or sodium hydrogen carbonate in a mixed solvent of water and a low-molecular-weight alcohol. Instead of the acetic acid, an inorganic acid like sulfuric acid or hydrochloric acid or an organic acid such as p-toluenesulfonic acid may be used in water alone or a low-molecular-weight alcohol alone such as methanol, or in a mixed solvent with an organic solvent.

[Reaction equation 4]

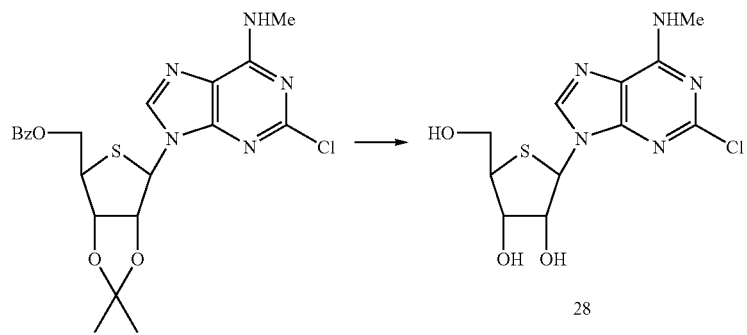

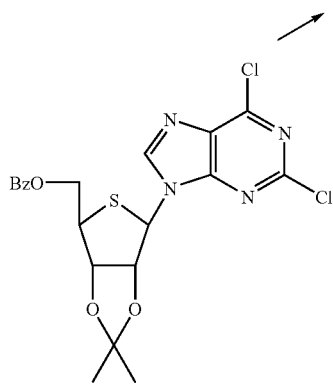

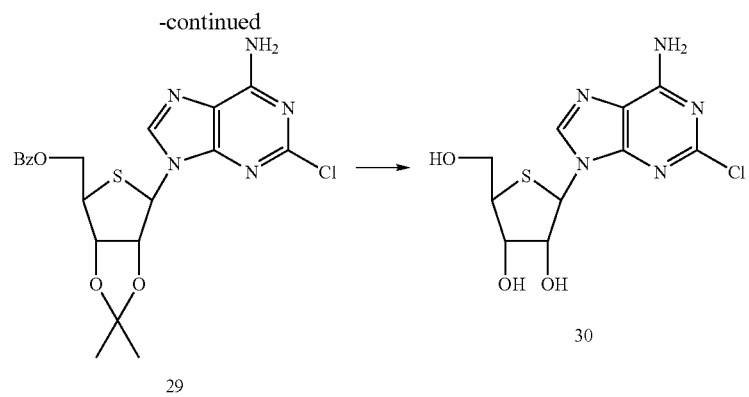

As shown in the above reaction equation 4, the manufacturing method of the compound having general formula (III) and the thionucleoside compound from the compound having chemical formula 21 as a starting material is described in reaction equation 4. $R_1$ is a hydroxymethyl group, $R_2$ is a methylamino group, and $R_3$ is a chloro group for the compound having the general formula (III), whereas $R_1$ is a hydroxymethyl group, $R_2$ is an amine group, and $R_3$ is a chloro group for the thionucleoside compound.

The compound having chemical formula 27 can be obtained by reacting the compound having chemical formula 21 with methylamine-tetrahydrofuran solution or an aqueous solution of methylamine. It is preferred to carry out the reaction in a closed container of metal or a special material. The compound having chemical formula 28 may be obtained from the compound resulting from the reaction of the compound having chemical formula 27 with an aqueous solution of acetic acid using the following methods, wherein an inorganic acid such as sulfuric acid or hydrochloric acid or an organic acid like p-toluenesulfonic acid may be used instead of acetic acid, in water or a low-molecular-weight alcohol alone as a solvent or in a mixed solvent with an organic solvent; by reacting with a metal alkoxide such as sodium methoxide or sodium ethoxide in a low molecular weight solvent like methanol or ethanol, or in a mixed solvent with an inert solvent such as dichloromethane or chloroform; by reacting with ammonia in an alcohol solvent like methanol or ethanol; or by reacting with an inorganic base like sodium carbonate or sodium hydrogen carbonate in a mixed solvent of water and a low-molecular-weight alcohol.

The compound having chemical formula 29 can be obtained by reacting the compound having chemical formula 21 with a saturated ammonia solution in a low-molecular-weight alcohol such as ethanol or methanol. It is also preferred to react with a saturated ammonia solution in 1,4-dioxane. The compound having chemical formula 30 can be obtained by the following methods from the compound resulting from the reaction of the compound having chemical formula 29 with an aqueous solution of acetic acid, or an inorganic acid such as sulfuric acid or hydrochloric acid or an organic acid like p-toluenesulfonic acid can be used instead of acetic acid, in water or a low-molecular-weight alcohol such as methanol alone, or in a mixed solvent with an organic solvent; by reacting with a metal alkoxide such as sodium methoxide or sodium ethoxide in a low-molecular-weight solvent or in a mixed solvent with an inert solvent such as dichloromethane or chloroform, by reacting with ammonia in an alcohol solvent such as methanol or ethanol, or by reacting with an inorganic base such as sodium carbonate or sodium hydrogen carbonate in a mixed solvent of water and a low-molecular-weight alcohol.

[Reaction equation 5]

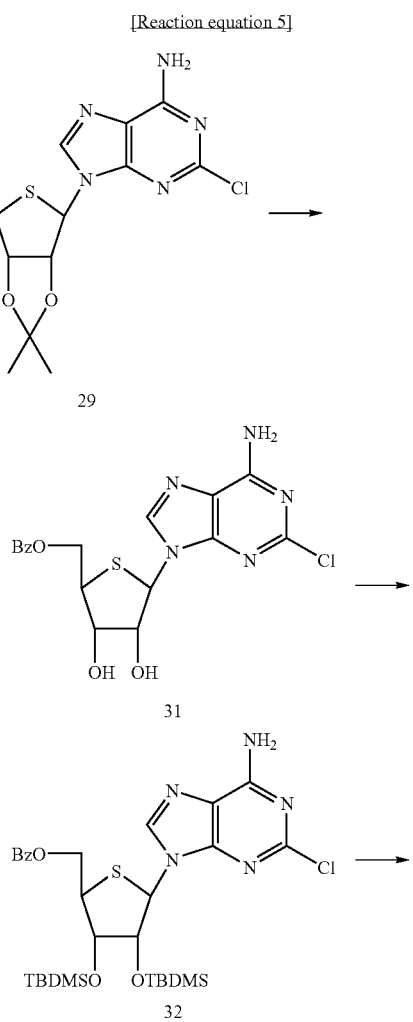

-continued

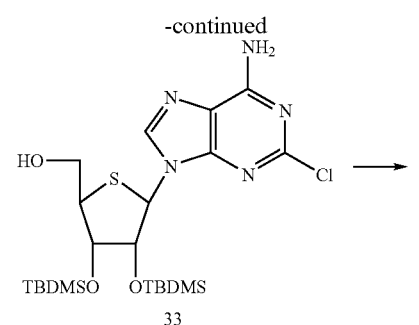

33

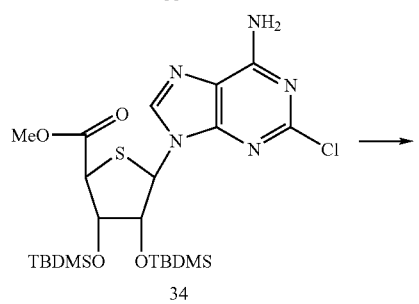

34

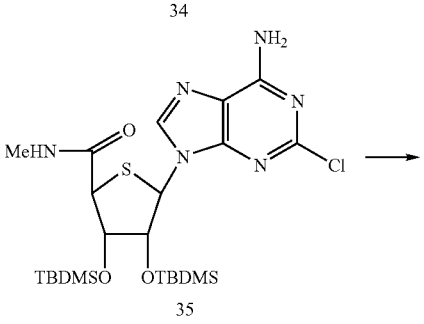

35

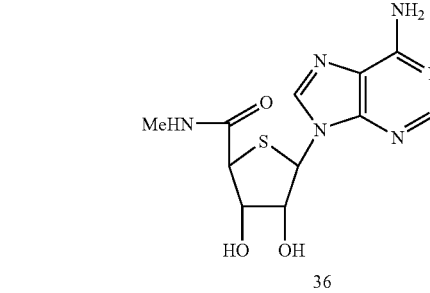

36

As shown in Reaction Equation 5, the compound having chemical formula 31 can be obtained from the reaction of the compound having chemical formula 29 with acetic acid, wherein an inorganic acid like sulfuric acid or hydrochloric acid or an organic acid such as p-toluenesulfonic acid may be used instead of acetic acid, in water or a low-molecular-weight alcohol such as methanol alone, or in a mixed solvent with an organic solvent. The compound having chemical formula 32 can be prepared by reacting the compound having chemical formula 31 with tert-butylchlorodimethylsilane in the presence of imidazole base, wherein an organic base such as triethylamine, pyridine, N,N-dimethylaminopyridine or 2,6-lutidine may be used instead of imidazole, and it is preferred to use an inert solvent such as N,N-dimethylaminoformamide, dichloromethane, tetrahydrofuran, or chloroform as a solvent.

The compound having chemical formula 33 can be obtained by reacting the compound having chemical formula 32 with a metal alkoxide such as sodium methoxide or sodium ethoxide in a low-molecular-weight alcohol such as methanol or ethanol or in a mixed solvent with an inert solvent like dichloromethane or chloroform; by reacting with ammonia in an alcohol solvent such as methanol or ethanol; or by reacting with an inorganic base such as sodium carbonate or sodium hydrogen carbonate in a mixed solvent of water and a low-molecular-weight alcohol. The compound having chemical formula 34 can be obtained by reacting dimethyl sulfate and potassium carbonate with the compound resulting from the reaction of the compound having chemical formula 33 with pyridinium dichromate in N,N-dimethylformamide solvent. Diazomethane or a methyl halide like methyl iodide may be used instead of dimethyl sulfate, whereas an inorganic base such as sodium carbonate or an organic base like DBU or n-butyllithium may be substituted for potassium carbonate. It is also possible to use acetone as a solvent or to use an organic solvent like tetrahydrofuran or dioxane.

The compound having chemical formula 35 can be obtained by reacting the compound having chemical formula 34 with methylamine solution in tetrahydrofuran or in water, wherein tetrahydrofuran alone may be used as a solvent or an inert solvent, like ethyl ether, petroleum ether, dichloromethane, tetrahydrofuran, or N,N-dimethylformamide may be mixed with water as a solvent. The compound having chemical formula 36 can be prepared by reacting the compound having chemical formula 35 with tetrabutylammonium fluoride, wherein a reagent that can generate a fluoride, such as triethylamine trihydrofluoride or hydrogen fluoride-pyridine, may be used instead of tetrabutyl ammonium fluoride. It is also desirable to use an organic acid like p-toluenesulfonic acid or an inorganic acid such as hydrochloric acid.

[Reaction equation 6]

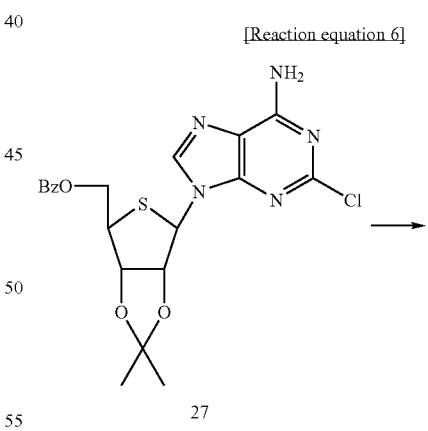

27

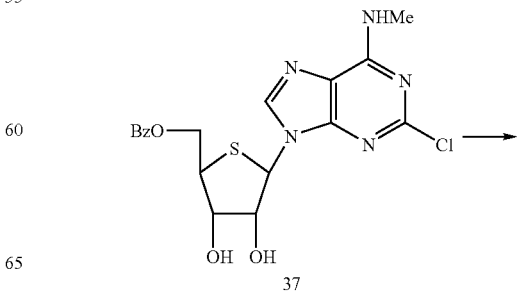

37

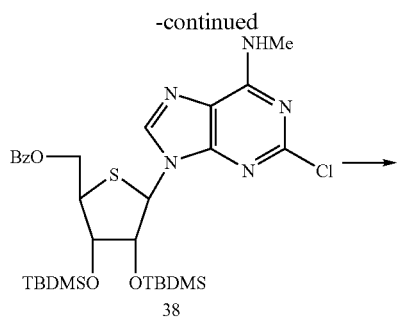
38

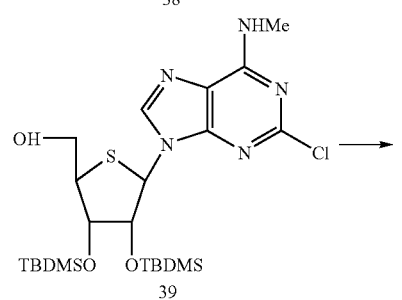
39

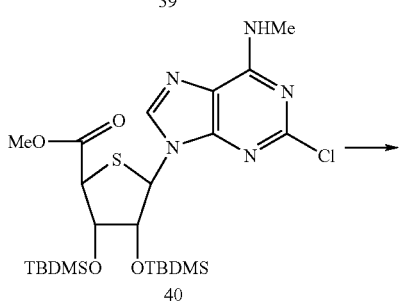
40

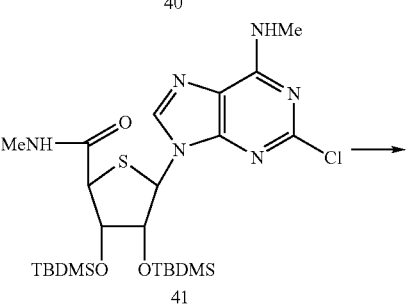
41

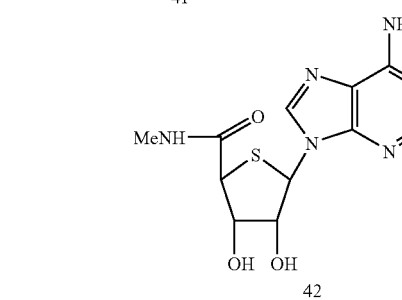
42

As shown in Reaction Equation 6, the compound having chemical formula 37 can be obtained by reacting the compound having chemical formula 27 with an aqueous solution of acetic acid, or with an inorganic acid such as sulfuric acid or hydrochloric acid or an organic acid like p-toluenesulfonic acid instead of acetic acid, in water or a low-molecular-weight alcohol like methanol alone, or in a mixed solvent with an organic solvent. The compound having chemical formula 38 can be obtained by reacting the compound having chemical formula 37 with tert-butylchlorodimethylsilane in the presence of imidazole base, wherein an organic base such as triethylamine, pyridine, N,N-dimethylaminopyridine, or 2,6-lutidine may be used instead of imidazole. It is preferred to use an inert solvent like N,N-dimethylaminoformamide, dichloromethane, tetrahydrofuran, or chloroform as a solvent.

The compound having chemical formula 39 can be prepared by reacting the compound having chemical formula 38 with a metal alkoxide such as sodium methoxide or sodium ethoxide in a low-molecular-weight alcohol such as methanol or ethanol, or in a mixed solvent with an inert solvent such as dichloromethane or chloroform; with ammonia in an alcohol solvent such as methanol or ethanol; or with an inorganic base such as sodium carbonate or sodium hydrogen carbonate in a mixed solvent of water and a low-molecular-weight alcohol. The compound having chemical formula 40 can be obtained by reacting dimethyl sulfate and potassium carbonate with the resulting compound from the reaction of the compound having chemical formula 39 with pyridinium dichromate in N,N-dimethylformamide. It is possible to use a methyl halide like methyl iodide or diazaomethane instead of dimethyl sulfate, whereas potassium carbonate may be replaced with an inorganic base such as sodium carbonate or an organic base such as DBU or n-butyllithium. Acetone may be used as a solvent or it is also possible to use an organic solvent like tetrahydrofuran or dioxane.

The compound having chemical formula 41 may be obtained from the reaction of the compound having chemical formula 40 with methylamine in tetrahydrofuran solution or in aqueous solution, wherein tetrahydrofuran alone may be used as a solvent, or an inert solvent such as ethyl ether, petroleum ether, dichloromethane, tetrahydrofuran, or N,N-dimethylformamide may be mixed with water as the solvent. The compound having chemical formula 42 can be obtained from the reaction of the compound having chemical formula 41 with tetrahydrobutylammonium fluoride. A reagent that can generate a fluoride such as triethylamine trihydrofluoride or hydrogen fluoride-pyridine may be used instead of tetrahydrobutylammonium fluoride, or it is also desirable to use an organic acid such as p-toluenesulfonic acid or an inorganic acid like hydrochloric acid.

[Reaction equation 7]

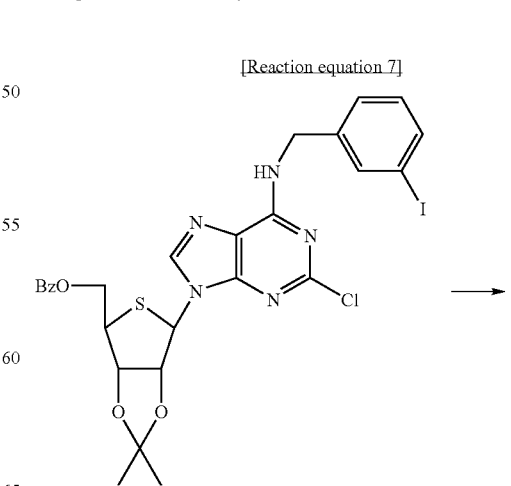
23

-continued

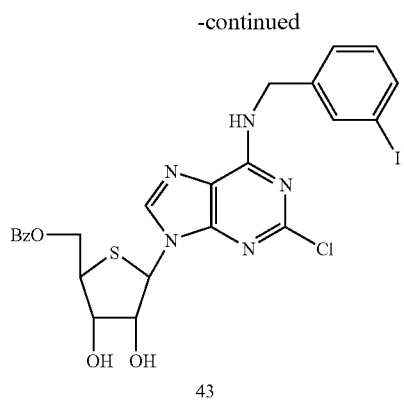
43

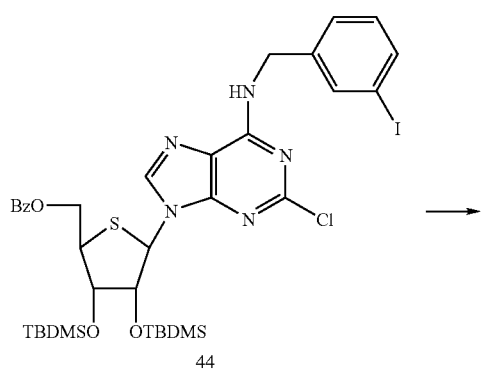
44

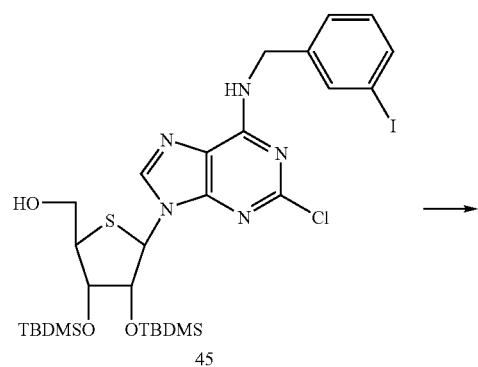
45

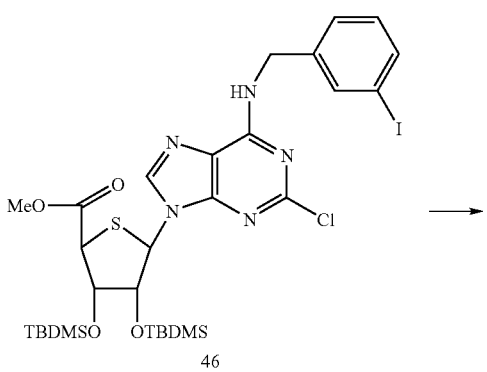
46

-continued

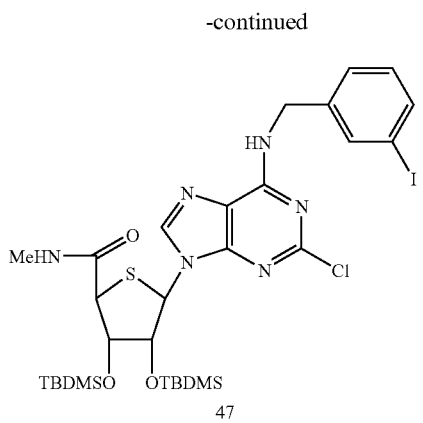
47

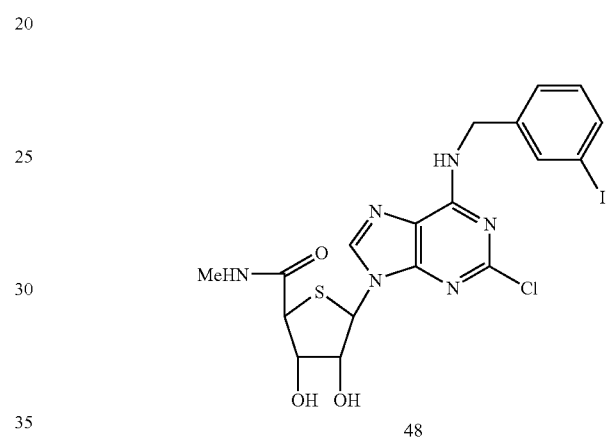
48

As shown in Reaction Equation 7, the compound having chemical formula 43 can be obtained by reacting the compound having chemical formula 23 with acetic acid or with an inorganic acid such as sulfuric acid or hydrochloric acid, or an organic acid like p-toluenesulfonic acid instead of acetic acid, in water or a low-molecular-weight alcohol such as methanol alone or in a mixed solvent with an organic solvent. The compound having chemical formula 44 may be obtained by reacting the compound having chemical formula 43 with tert-butylchlorodimethylsilane in the presence of imidazole base, wherein an organic base such as triethylamine, pyridine, N,N-dimethylaminopyridine or 2,6-lutidine may also be used instead of imidazole. It is desirable to use an inert solvent like N,N-dimethylaminoformamide, dichloromethane, tetrahydrofuran, or chloroform as a solvent.

The compound having chemical formula 45 can be obtained by reacting the compound having chemical formula 44 with a metal alkoxide such as sodium methoxide or sodium ethoxide in a low-molecular-weight alcohol solvent such as methanol or ethanol or in a mixed solvent with an inert solvent such as dichloromethane or chloroform; or by reacting with ammonia in an alcohol solvent such as methanol or ethanol; or by reacting with an inorganic base such as sodium carbonate or sodium hydrogen carbonate in a mixed solvent of water and a low-molecular-weight alcohol.

The compound having chemical formula 46 can be obtained by reacting dimethyl sulfate in the presence of potasssium carbonate with the compound resulting from the reaction of the compound having chemical formula 45 with pyridinium dichromate in N,N-dimethylformamide solvent. Dimethyl sulfate may be replaced with a methyl halide such as methyl iodide or diazomethane, whereas it is possible to use an inorganic base like sodium carbonate or an organic base such as DBU or n-butyllithium instead of potassium carbonate. Acetone may be used as a solvent, and it is also possible to mix water with an inert solvent like ethyl ether, petroleum ether, dichloromethane, tetrahydrofuran, or N,N-dimethylformamide.

The compound having chemical formula 48 can be obtained by reacting the compound having chemical formula 47 with tetrabutylammonium fluoride, wherein a reagent that can generate a fluoride, like triethylamine trihydrofluoride or hydrogen fluoride-pyridine, may be used instead of tetrabutylammonium fluoride, or it is preferred to use an organic acid such as p-toluenesulfonic acid or an inorganic acid like hydrochloric acid.

The compound of the present invention has an asymmetric carbon, and therefore the racemic mixture of the aforementioned general formula (I) and R and S stereoisomers are also included in the scope of the present invention. The present invention also includes the pharmaceutically acceptable salts of the compound.

The pharmaceutically acceptable salts of the aforementioned general formula (I) include salts of the acidic or basic group that can be present in the compound of the general formula (I), unless indicated otherwise. For example, the pharmaceutically acceptable salts include sodium, calcium, and potassium salts of the hydroxyl group, whereas other pharmaceutically acceptable salts of the amino group are hydrobromide, sulfate salt, hydrogen sulfate salt, phosphate salt, hydrogen phosphate salt, dihydrogen phosphate salt, acetate, succinate, citrate, tartrate, lactate, mandelate, methanesulfonate (mesylate), and p-toluenesulfonate (tosylate) salt. These salts can be manufactured using manufacturing methods of salts known in the corresponding industry.

The compound of the aforementioned general formula (I) has an asymmetric center, and therefore exists in different mirror-image isomers. All optical isomers and stereoisomers of the compound having general formula (I) and their mixtures are included within the scope of the present invention. The present invention includes application of racemic isomers, more than one mirror image isomer, more than one partial stereoisomer, or their mixtures. The present invention also includes separation methods or manufacturing methods of isomers that are known in the corresponding industry.

The present invention further provides a pharmacological composition comprising an effective amount of the compound having the aforementioned general formulas (I)–(IV) and the pharmacutically acceptable carrier, auxiliary material, or diluent.

The aforementioned cancer includes lung cancer, bone cancer, pancreatic cancer, skin cancer, head or neck cancer, melanosis or melanosis bulbi, uterine cancer, ovarian cancer, rectal cancer, stomach cancer, periproctic cancer, colon cancer, breast cancer, cancerous Fallopian tube tumor, cancerous endometrioma, cancerous cervical tumor, cancerous vaginal tumor, cancerous vulval tumor, Hodgkin's disease, cancer of the esophagus, small intestine cancer, cancer of the endocrine glands, thyroid cancer, parathyroid cancer, adrenal cancer, soft tissue sarcoma, urethral cancer, phallus cancer, prostate cancer, chronic or acute leukemia, lymphocytic lymphoma, bladder cancer, kidney or ureter cancer, cancerous renal tumor, cancerous tumor of the renal pelvis, tumor in central nervous system (CNS), primary CNS lymphoma, myeloma, nerve tumor in brain stem, pituitary gland adenoma, or combinations of two or more of these cancers.

The aforementioned inflammation includes ulcerative inflammation, exudative inflammation, purulent inflammation, hemorrhagic inflammation, and hyperplastic inflammation.

In addition, the present invention provides a composition for prevention and treatment of cancer or inflammatory diseases, which composition contains the compound of the aforementioned general formula (I) as an active ingredient and the pharmaceutically acceptable carrier.

For example, the compound of the present invention may be dissolved in an oil, propylene glycol, or other solvent that is conventionally used for manufacturing injectable solutions. Appropriate carriers are not specifically limited, but include saline solution, polyethylene glycol, ethanol, vegetable oil, and isopropyl myristate. For topical application, the compound of the present invention may be formulated as an ointment or cream.

The formulation methods and formulating agents are described below, however, they are not limited to these examples.

As a pharmacological formulation of the compound of the present invention, pharmaceutically acceptable salts of the compound may be used, alone or in an appropriate combination, including combinations with other pharmaceutically active ingredients.

The compound of the present invention may be dissolved, suspended, or emulsified in an aqueous solvent of saline and 5% dextrose or in a nonaqueous solvent such as vegetable oil, synthetic fatty acid glyceride, high-molecular-weight fatty acid ester, or propylene glycol to formulate an injectable solution. The formulation of the present invention may include additives like disintegrants, isotonic agents, suspending agents, emulsifiers, stabilizers, and preservatives.

An ideal dose of the compound of the present invention depends on the condition and weight of the patient, severity of the disease, drug type, and administration route and period, but may be selected properly by the corresponding professionals. However, it is preferred to administer the compound of the present invention at a daily dose of 0.001–100 mg/kg body weight, more preferably 0.01–30 mg/kg body weight. The administration may be done once or several times a day. The composition may contain the compound of the present invention at a level of 0.0001–10 wt % of the total amount of the entire composition, more preferably 0.001–1 wt %.

The pharmaceutical composition of the present invention may be administered via various routes to mammals like rats, mice, domestic animals, and humans. It is anticipated that all administration methods can be allowed. For example, oral, rectal, intravenous, intramuscular, intrathecal, intra-arterial, hypodermic, intrauterine, epidural or intracerebroventricular injection may be administered.

The compounds of the present invention are useful in the manufacture of a medicament for the treatment of cancer or inflammatory disease, state, or condition.

The present invention further provides a method for treating or preventing in an animal, e.g., a human, a disease, state, or condition which is responsive to agonizing or antagonizing an $A_3$ adenosine receptor comprising administering to the animal an effective amount of a compound of formulas (I)–(IV). The disease, state, or condition is cancer, e.g., lung cancer or skin cancer, or inflammation. The present invention provides compounds of formulas (I)–(IV) for use in medicine. Embodiments of formulas I and II show $A_3$ antagonistic properties and embodiments of formulas II and IV show $A_3$ agonistic property.

The following examples further illustrate the invention but, of course, should not be construed as in any way limiting its scope.

EXAMPLES

This example demonstrates methods of preparing embodiments of the nucleosides of the present invention.

Experimental Example 1

Preparation of (2R,3S,4S,5R)-2,3:5,6-di-O-isopropylidene-D-gulono-1,4-lactone compound (1)

20.2 g of D-gulonic γ-lactone (0.114 mol) and 27 g of anhydrous copper(II) sulfate (0.170 mol) were suspended in 0.65 L of dry acetone at ambient temperature, and 1.7 mL of concentrated sulfuric acid were added, which was then stirred for 24 h. The acidity was adjusted to 7 with calcium hydroxide, and then precipitated solids were filtered off. The resulting filtrate was concentrated under reduced pressure to obtain 28.7 g of (2R,3S,4S,5R)-2,3:5,6-di-O-isopropylidene-D-gulono-1,4-lactone compound (yield: 98%) as an oil, which was used immediately for the next reaction.

Experimental Example 2

Preparation of {(4R)-(2,2-dimethyl[1,3]dioxolan-4-yl)}-{(4R,5S)-(5-hydroxymethyl-2,2-dimethyl[1,3]dioxolan-4-yl)}-(S)-methanol compound (2)

25.1 g (0.097 mol) of (2R,3S,4S,5R)-2,3:5,6-di-O-isopropylidene-D-gulono-1,4-lactone compound (1) from the aforementioned Experimental Example 1 were dissolved in 450 mL of ethyl ether to which 7.2 g (0.190 mol) of lithiumaluminum hydride were carefully added in several portions. The reaction solution was stirred at ambient temperature for 10 h, and 7.2 mL of water, 7.2 mL of 15% aqueous sodium hydroxide solution, 22 mL of water, and 19 g of anhydrous magnesium sulfate were sequentially added at 0° C. The resulting solution was filtered and the filtrate was concentrated under reduced pressure. The concentrate was purified by silica gel column chromatography using the eluant hexane:ethyl acetate=1:1.24.1 g (yield: 95%) of {(4R)-(2,2-dimethyl[1,3]dioxolan-4-yl)}-{(4R,5S)-(5-hydroxymethyl-2,2-dimethyl[1,3]dioxolan-4-yl)}-(S)-methanol were obtained as an oil.

$^1$H-NMR(CDCl$_3$) δ: 1.29 (d, 6H), 1.36 (s, 3H), 1.43 (s, 3H), 3.26 (s, 1H), 3.28 (s, 1H), 3.36–3.79 (m, 4H), 3.96–4.03 (m, 2H), 4.12–4.22 (m, 2H)

Experimental Example 3

Preparation of methanesulfonic acid {(4R)-(2,2-dimethyl[1,3]dioxolan-4-yl)}-{(4S,5S)-(5-methanesulfonyloxymethyl-2,2-dimethyl[1,3]dioxolan-4-yl)}-(S)-methyl ester compound (3)

4.1 g (0.016 mol) of {(4R)-(2,2-dimethyl[1,3]dioxolan-4-yl)}-{(4R,5S)-(5-hydroxymethyl-2,2-dimethyl[1,3]dioxolan-4-yl)}-(S)-methanol from the aforementioned Experimental Example 2 were dissolved in a mixed solvent of 1.0 L dichloromethane and 25 mL pyridine. After cooling the mixture to 0° C., 18 mL (0.236 mol) of methanesulfonyl chloride were added and the resulting solution was stirred for 5 h at 0° C. Saturated sodium bicarbonate solution was added and the compound was extracted with chloroform. The extract was dried, filtered, and concentrated under reduced pressure. The concentrate was purified by silica gel column chromatography using the eluant hexane:ethyl acetate=2:1 to obtain 6.4 g (yield: 98%) of methanesulfonic acid {(4R)-(2,2-dimethyl[1,3]dioxolan-4-yl)}-{(4S,5S)-(5-methanesulfonyloxymethyl-2,2-dimethyl[1,3]dioxolan-4-yl)}-(S)methyl ester as an oil.

$^1$H-NMR(CDCl$_3$) δ:1.37 (s, 3H), 1.39 (s, 3H), 1.46 (s, 3H), 1.52 (s, 3H), 3.10 (s, 3H), 3.18 (s, 3H), 3.92–408 (m, 1H), 4.08–4.20 (m, 2H), 4.39–4.49 (m, 4H), 4.81–4.87 (m, 1H)

Experimental Example 4

Preparation of (3aS,4R,6aR)-4-((4R)-2,2-dimethyl [1,3]dioxolan-4-yl)-2,2-dimethyltetrahydrothieno[3,4-d][1,3]dioxole compound (4)

10.1 g (0.024 mol) of methanesulfonic acid {(4R)-(2,2-dimethyl[1,3]dioxolan-4-yl)}-{(4S,5S)-(5-methanesulfonyloxymethyl-2,2-dimethyl[1,3]dioxolan-4-yl)}-(S)methyl ester from the aforementioned Experimental Example 3 were dissolved in 260 mL of N,N-dimethylformamide, and 8.9 g (0.036 mol) of sodium sulfide were added. The reaction mixture was reacted at 100° C. for 3 h. The reaction mixture was concentrated under reduced pressure, and water was added to the concentrate, which was then extracted with ethyl acetate. The organic layer was dried and filtered, and the filtrate was concentrated under reduced pressure. The concentrate was purified by silica gel column chromatography using the eluant (hexane:ethyl acetate=5:1) to obtain 5.9 g (yield: 94%) of (3aS,4R,6aR)-4-((4R)-2,2-dimethyl[1,3] dioxolan-4-yl)-2,2-dimethyltetrahydrothieno[3,4-d][1,3]dioxole as an oil.

$^1$H-NMR (CDCl$_3$) δ: 1.33 (d, 6H), 1.44 (s, 3H), 1.51 (s, 3H), 2.86 (d, 1H), 3.09 (m, 1H), 3.22, (s, 1H), 3.76 (dd, 1H), 3.98 (m, 1H), 4.15 (dd, 1H), 4.93 (d, 2H).

Experimental Example 5

Preparation of (1R)-1-(3aS,4R,6aR)-2,2-dimethyltetrahydrothieno[3,4-d][1,3]dioxol-4-yl)ethane-1, 2-diol compound (5)

5.4 g (0.020 mol) of (3aS,4R,6aR)-4-((4R)-2,2-dimethyl [1,3]dioxolan-4-yl)-2,2-dimethyltetrahydrothieno[3,4-d][1, 3]dioxole obtained from the aforementioned Experimental Example 4 were added to 150 mL of 60% aqueous acetic acid solution, which was stirred at ambient temperature for 50 h. The reaction mixture was concentrated under reduced pressure, and the concentrate was purified by silica gel column chromatography using the eluant (hexane:ethyl acetate=1:1) to obtain 3.4 g (yield: 75%) of (1R)-1-((3aS, 4R,6aR)-2,2-dimethyltetrahydrothieno[3,4-d][1,3]dioxol-4-yl)ethane-1,2-diol as an oil.

$^1$H-NMR(CDCl$_3$) δ: 1.34 (s, 3H), 1.53 (s, 3H), 2.90 (dd, 1H), 3.09 (dd, 1H) 3.27 (dd, 1H), 3.58–3.65 (m, 2H), 3.69 (dd, 1H), 3.79 (dd, 1H), 4.15 (dd, 1H), 4.93 (m, 2H)

Experimental Example 6

Preparation of (3aS,4S,6aR)-2,2-dimethyltetrahydrothieno[3,4-d][1,3]dioxole-4–Carbaldehyde compound (6)

2.5 g (11.2 mmol) of (1R)-1-((3aS,4R,6aR)-2,2-dimethyltetrahydrothieno[3,4-d][1,3]dioxol-4-yl)-ethane-1,2-diol from the aforementioned Experimental Example 5 were dissolved in ethyl acetate to which lead tetraacetate were added at 0° C., and the reaction mixture was stirred for 10 min. The reaction mixture was filtered. Ethyl acetate was added to the filtrate, which was washed with saturated sodium bicarbonate, dried, and filtered. The filtrate was concentrated under reduced pressure, and the concentrate was purified by silica gel column chromatography using the eluant (hexane:ethyl acetate=5:1) to obtain 2.1 g (yield: 98%) of (3aS,4S,6aR)-2,2-dimethyltetrahydrothieno[3,4-d][1,3]dioxole-4–Carbaldehyde as an oil.

$^1$H-NMR(CDCl$_3$) δ: 1.33 (s, 3H), 1.52 (s, 3H), 2.61 (dd, 1H), 2.87 (dd, 1H) 3.92 (s, 1H), 4.92 (t, 1H), 5.10 (d, 1H), 9.43 (s, 1H),

Experimental Example 7

Synthesis of (3aS,4S,6aR)-2,2-dimethyltetrahydrothieno[3,4-d][1,3]dioxole-4-carboxylic acid methyl ester compound (7)

2.8 g (0.015 mol) of (3aS,4S,6aR)-2,2-dimethyltetrahydrothieno[3,4-d][1,3]dioxole-4–Carbaldehyde from the aforementioned Experimental Example 6 were dissolved in 200 mL of anhydrous N,N-dimethylformamide to which 26.7 g (0.070 mol) of pyridinium dichromate was added. The reaction mixture was stirred at ambient temperature for 20 h. After 0.3 L of water were added, it was extracted with 2.5 L of ethyl acetate (0.5 L×5). The extract was dried, filtered, and concentrated under reduced pressure to obtain the concentrate which was (3aS,4S,6aR)-2,2-dimethyltetrahydrothieno[3,4-d][1,3]dioxole-4-carboxylic acid. The concentrate was dissolved in 65 mL of acetone to which 2 mL (21.14 mmol) of dimethyl sulfate and 1.2 g (8.68 mmol) of potassium carbonate were added. The resulting mixture was stirred for 2 h. Acetone was distilled off under reduced pressure, and the residue was dissolved in ethyl acetate, followed by washing with water and saturated saline solution. The organic layer was dried and filtered, and the filtrate was concentrated under reduced pressure. The concentrate was purified by silica gel column chromatography using the eluant (hexane:ethyl acetate=3:1) mixture to obtain 2.5 g (yield: 78%) of (3aS,4S,6aR)-2,2-dimethyltetrahydrothieno[3,4-d][1,3]dioxole-4-carboxylic acid methyl ester as an oil.

$^1$H-NMR(CDCl$_3$) δ: 1.33 (s, 3H), 1.52 (s, 3H), 2.92 (d, 1H), 3.19 (dd, 1H) 3.72 (s, 3H), 3.80 (s, 1H), 4.99 (m, 2H)

Experimental Example 8

Synthesis of (3aS,4R,6aR)-2,2-dimethyltetrahydrothieno[3,4-d][1,3]dioxole-4-carboxylic acid methyl amide compound (8)

1.1 g (0.005 mol) of (3aS,4R,6aR)-2,2-dimethyltetrahydrothieno[3,4-d][1,3]dioxole-4-carboxylic acid methyl ester compound (7) from the aforementioned Experimental Example 7 were dissolved in 40 mL (0.080 mol) of 2N methylamine solution in tetrahydrofuran, which was stirred at 50° C. for 24 h in a sealed container. After concentration under reduced pressure, the obtained concentrate was purified by silica gel column chromatography using the eluant (hexane:ethyl acetate=2:1) to obtain 953 mg (yield: 87%) of (3aS,4S,6aR)-2,2-dimethyltetrahydrothieno[3,4-d][1,3]dioxole-4-carboxylic acid methyl amide as an oil.

$^1$H-NMR(CDCl$_3$) δ: 1.29 (s, 3H), 1.48 (s, 3H), 2.78 (d, 3H), 2.91 (d, 1H) 3.04 (dd, 1H), 3.72 (s, 1H), 4.91 (t, 1H), 5.21 (d, 1H), 6.65 (brs, 1H)

Experimental Example 9

Synthesis of (3aS,4S,5R,6aR) and (3aS,4S,5S,6aR)-2,2-dimethyl-5-oxotetrahydro-5λ$^4$-thieno[3,4-d][1,3]dioxole-4-carboxylic acid methyl amide compound (9)

120 mg (0.55 mmol) of (3aS,4R,6aR)-2,2-dimethyltetrahydrothieno[3,4-d][1,3]dioxole-4-carboxylic acid methyl amide from the aforementioned Experimental Example 8 were dissolved in 15 mL of dichloromethane. After cooling to −78° C., 110 mg (0.55 mmol, 80% reagent) of m-chloroperbenzoic acid dissolved in 5 mL of dichloromethane were added slowly. The reaction mixture was stirred at −78° C. for 45 min, and saturated sodium bicarbonate solution was added, followed by extraction with dichloromethane. The organic layer was washed with saturated saline solution, dried, filtered, and concentrated under reduced pressure. The resulting concentrate was purified by silica gel column chromatography using the eluant (hexane:ethyl acetate=1:1.2) to obtain 125 mg (yield: 97%) of (3aS,4S,5R,6aR)- and (3aS,4S,5S,6aR)-2,2-dimethyl-5-oxotetrahydro-5λ$^4$-thieno[3,4-d][1,3]dioxole-4-carboxylic acid methyl amide as an oil.

$^1$H-NMR(CDCl$_3$) δ: 1.23 (s, 3H), 1.37 (s, 3H), 2.80 (d, 3H), 3.21 (dd, 1H), 3.61 (d, 1H), 4.30 (s, 1H), 5.06 (m, 2H), 7.12 (br s, 1H)

Experimental Example 10

Synthesis of (3aS,4R,6aR)-4-(2,6-dichloropurin-9-yl)-2,2-dimethyltetrahydrothieno[3,4-d][1,3]dioxole-4-carboxylic acid methyl amide compound (10)

102 mg (0.54 mmol) of 2,6-dichloropurine and 20 mg (0.15 mmol) of ammonium sulfate were suspended in 10 mL of anhydrous hexamethyldisilazane and stirred under reflux for 6 h. The reaction mixture was concentrated under reduced pressure and dry conditions, and the concentrate was dissolved in 8 mL of dichloroethane. 110 mg (0.47 mmol) of (3aS,4S,5R,6aR)- and (3aS,4S,5S,6aR)-2,2-dimethyl-5-oxotetrahydro-5λ$^4$-thieno[3,4-d][1,3]dioxole-4-carboxylic acid methyl amide dissolved in 5 mL of dichloroethane were added, followed by cooling to −10° C. After adding 0.10 mL (0.54 mmol) of trimethylsilyltrifluoromethanesulfonate, the reaction mixture was stirred at −10° C. for 20 min, and then stirred under reflux for 4 h. Saturated sodium bicarbonate solution was added and the mixture stirred for 15 min, followed by extraction with dichloromethane. The extract was washed with saturated saline solution, dried, filtered, and concentrated under reduced pressure. The concentrate was purified by silica gel column chromatography using the eluant (hexane:ethyl acetate=1.5:1) to obtain 103 mg (yield: 54%) of (3aS,4R, 6aR)-4-(2,6-dichloropurin-9-yl)-2,2-dimethyltetrahydrothieno[3,4-d][1,3]dioxole-4-carboxylic acid methyl amide as an oil.

$^1$H-NMR(CDCl$_3$) δ: 1.42 (s, 3H), 1.61 (s, 3H), 2.83 (d, 3H), 3.07 (m, 2H) 5.11 (m, 1H), 6.09 (d, 1H), 7.24 (br s, 1H), 8.52 (s, 1H) UV (methanol): λ$_{max}$ 270 nm (pH 7).

Experimental Example 11

Synthesis of (3aS,4R,6aR)-4-[2-chloro-6-(3-iodo-benzylamino)purin-9-yl)]-2,2-dimethyltetrahydrothieno[3,4-d][1,3]dioxole-4-carboxylic acid methyl amide compound (11)

65 mg (0.16 mmol) of (3aS,4R,6aR)-4-(2,6-dichloropurin-9-yl)-2,2-dimethyltetrahydrothieno[3,4-d][1,3]dioxole-4-carboxylic acid methyl amide from the aforementioned Experimental Example 10, 55 mg (0.20 mmol) of 3-iodobenzylamine hydrochloride, and 0.065 mL (0.46 mmol) of triethylamine were added to ethanol and stirred at ambient temperature for 3 days. The reaction mixture was distilled under reduced pressure to obtain a concentrate. The concentrate was purified by silica gel column chromatography using the eluant (hexane:ethyl acetate=1:1) to obtain 87 mg (yield: 90%) of (3aS,4R,6aR)-4-[2-chloro-6-(3-iodobenzylamino)purin-9-yl)]-2,2-dimethyltetrahydrothieno[3,4-d][1,3]dioxole-4-carboxylic acid methyl amide as a white foam.

$^{1}$H-NMR(CDCl$_{3}$) δ: 1.43 (s, 3H), 1.61 (s, 3H), 2.88 (d, 3H), 3.07 (d, 2H) 4.73 (br d, 2H), 5.09 (m, 1H), 6.11 (d, 1H), 6.49 (br s, 1H), 7.07 (t, 1H), 7.32 (d, 1H), 7.60 (d, 1H), 7.72 (s, 1H), 8.16 (s, 1H)

UV (methanol): λ$_{max}$ 271 nm (pH 7).

Experimental Example 12

Synthesis of (2R,3S,4R)-2-[2-chloro-6-(3-iodobenzylamino)purin-9-yl)]-3,4-dihydroxytetrahydrothiophene-2-carboxylic acid methyl amide compound (12)

4 mL of 80% aqueous acetic acid solution were added to 42 mg (0.07 mmol) of (3aS,4R, 6aR)-4-[2-chloro-6-(3-iodobenzylamino)purin-9-yl]-2,2-dimethyltetrahydrothieno[3,4-d][1,3]dioxole-4-carboxylic acid methyl amide from the aforementioned Experimental Example 11, which was then stirred at 55° C. for 12 h. The reaction mixture was distilled under reduced pressure, and then the pH of the concentrate was adjusted to neutral by adding a saturated ammonia methanol solution. The concentrate was purified by silica gel column chromatography using the eluant (dichloromethane and methanol=7:1) to obtain 20 mg (yield: 52%) of (2R,3S,4R)-2-[2-chloro-6-(3-iodobenzylamino)purin-9-yl)-3,4-dihydroxytetrahydrothiophene-2-carboxylic acid methyl amide as white solids (see Table 1).

Melting point: 205–207° C.

[α]$^{26}$$_{D}$: −24.5 (c 0.06, methanol)°

ν$_{max}$ (KBr)/cm$^{-1}$: 1066, 1375, 1455, 2924

1H-NMR (DMSO-d$_{6}$) δ: 2.63 (d, 3H), 2.99 (m, 1H), 3.15 (m, 1H), 4.21 (br s, 1H), 4.73 (br d, 2H), 5.03 (br s, 1H), 5.68 (d, 1H), 6.45 (d, 1H), 7.12 (t, 1H), 7.33 (d, 1H), 7.58 (d, 1H), 7.73 (s, 1H), 8.13 (s, 1H), 8.25 (br s, 1H) 8.73 (br s, 1H)

UV (methanol): λ$_{max}$ 271 nm (pH 7).

TABLE 1

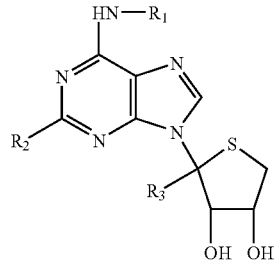

(II)

| Compound group | Compound | R$_1$ | R$_2$ | R$_3$ | R'$_3$ | Spectral data |
|---|---|---|---|---|---|---|
| II | 12 | 3-Iodobenzyl | Chlorine | Methylaminocarbonyl | Hydrogen | $^{1}$H-NMR(DMSO-d6) δ: 2.63(d, 3H), 2.99(m, 1H), 3.15(m, 1H), 4.21 (br s, 1H), 4.73, (br d, 2H), 5.03(br s, 1H), 5.68(d, 1H), 6.45(d, 1H), 7.12(t, 1H), 7.33 (d, 1H), 7.58(d, 1H), 7.73(s, 1H) 813(s, 1H), 8.258(br s, 1H), 8.73(brs, 1H) |

Experimental Example 13

Synthesis of (3aS,4R,6aR)-2,2-dimethyltetrahydrothieno[3,4-d][1,3]dioxol-4-yl)-methanol compound (13)

5.6 g (30.0 mmol) of (3aS,4S,6aR)-2,2-dimethyltetrahydrothieno[3,4-d][1,3]dioxole-4–Carbaldehyde were dissolved in 70 mL of methanol to which 1.3 g (33.6 mmol) of sodium borohydride were added in several portions at 0° C. The reaction mixture was stirred for 30 min at ambient temperature and neutralized with acetic acid. After distillation under reduced pressure, saturated saline solution was added and the product was extracted with ethyl acetate. The extract was dried and filtered. The filtrate was distilled under reduced pressure to obtain a concentrate. The concentrate was purified by silica gel column chromatography using the eluant (hexane:ethyl acetate=2:1) to obtain 5.5 g (yield; 98%) of (3aS,4R,6aR)-2,2-dimethyltetrahydrothieno[3,4-d][1,3]dioxol-4-yl) methanol as white foam.

¹H-NMR(CDCl₃)S: 1.33 (s, 3H), 1.53 (s, 3H), 2.41 (br s, 1H), 2.89 (dd, 1H), 3.09 (dd, 1H), 3.44 (dt, 1H), 3.59 (d, 2H), 4.71 (dd, 1H), 4.91 (dt, 1H)

Experimental Example 14

Synthesis of benzoic acid (3aS,4R,6aR)-2,2-dimethyltetrahydrothieno[3,4-d][1,3]dioxol-4-yl methyl ester compound (14)

2.1 g (11.1 mmol) of (3aS,4R,6aR)-2,2-dimethyltetrahydrothieno[3,4-d][1,3]dioxol-4-yl)-methanol from the aforementioned Experimental Example 13 were dissolved in 20 mL of pyridine to which 1.9 g (13.4 mmol) of benzoyl chloride were added at 0° C. The reaction mixture was stirred at ambient temperature for 6 h, and then 2 mL of methanol were added. After distillation of the reaction mixture under reduced pressure, 50 mL of diethyl ether were added and the solids formed were filtered. The filtrate was distilled under reduced pressure to obtain the concentrate. The concentrate was purified by silica gel column chromatography using the eluant (hexane:ethyl acetate=4:1) to obtain 3.2 g (yield: 99%) of benzoic acid (3aS,4R,6aR)-2,2-dimethyltetrahydrothieno[3,4-d][1,3]dioxol-4-yl methyl ester as a colorless oil.

¹H-NMR(CDCl₃) δ: 1.26 (s, 3H), 1.47 (s, 3H), 2.87 (dd, 1H), 3.09 (dd, 1H), 3.44 (dt, 1H), 4.28 (m, 2H), 4.72 (dd, 1H), 4.91 (dt, 1H), 7.35–7.99 (m, 5H)

Experimental Example 15

Synthesis of benzoic acid (3aS,4R,5R,6aR)-(3aS,4R,5S,6aR)-2,2-dimethyl-5-oxotetrahydro-5λ⁴-thieno[3,4-d][1,3]dioxol-4-yl methyl ester compound (15)

1.4 g (4.6 mmol) of benzoic acid (3aS,4R,6aR)-2,2-dimethyltetrahydrothieno[3,4-d][1,3]dioxol-4-yl methyl ester from the aforementioned Experimental Example 14 were dissolved in 30 mL of dichloromethane. After cooling the reaction mixture to −78° C., 1.0 g (4.6 mmol) of m-chloroperbenzoic acid solution in 15 mL of dichloromethane was added dropwise, and the reaction mixture was stirred at −78° C. for 45 min. Saturated sodium bicarbonate solution was added and the product was extracted with dichloromethane. The organic layer was washed with saturated saline solution, dried, and filtered. The filtrate was distilled under reduced pressure, and the concentrate was purified by silica gel column chromatography using the eluant (hexane:ethyl acetate=2:1) to obtain 3.2 g (yield: 99%) of benzoic acid (3aS,4R,5R,6aR)-(3aS,4R,5S,6aR)-2,2-dimethyl-5-oxotetrahydro-5λ⁴-thieno[3,4-d][1,3]dioxol-4-yl methyl ester as a solid.

¹H-NMR(CDCl₃) δ: 1.33 (s, 3H), 1.49 (s, 3H), 3.21 (dd, 1H), 3.37 (dd, 1H), 3.47 (m, 1H), 4.72 (dd, 1H), 4.87 (dd, 1H), 5.02 (t, 1H), 5.24 (m, 1H), 7.41–8.03 (m, 5H)

Experimental Example 16

Synthesis of benzoic acid (3aS,4R,6R,6aR)-(3aS,4R,6S,6aR)-6-acetoxy-2,2-dimethyltetrahydrothieno[3,4-d][1,3]dioxol-4-yl methyl ester compound (16)

3.5 g (11.3 mmol) of benzoic acid (3aS,4R,5R,6aR)-(3aS,4R,5,6aR)-2,2-dimethyl-5-oxotetrahydro-5λ⁴-thieno[3,4-d][1,3]dioxol-4-yl methyl ester from the aforementioned Experimental Example 15 were dissolved in 90 mL of acetic anhydride, followed by stirring at 100° C. for 6 h. After the reaction mixture was concentrated under reduced pressure, water was added and the product was extracted with ethyl acetate. The organic layer was washed with saturated sodium bicarbonate and then saturated saline solution. The organic layer was dried, filtered, and distilled under reduced pressure to obtain the concentrate. The concentrate was purified by silica gel column chromatography using the eluant (hexane:ethyl acetate=3:1) to obtain 2.5 g (yield: 62%) of benzoic acid (3aS,4R,6R,6aR)-(3aS,4R,6S,6aR)-6-acetoxy-2,2-dimethyltetrahydrothieno[3,4-d][1,3]dioxol-4-yl methyl ester.

¹H-NMR(CDCl₃) δ: 1.30 (s, 3H), 1.50 (s, 3H), 2.03 (s, 3H), 3.76 (dd, 1H), 4.39 (m, 2H), 4.94 (d, 1H), 4.98 (d, 1H), 6.06 (s, 1H), 7.42–8.06 (m, 5H)

Experimental Example 17

Synthesis of benzoic acid (3aS,4R,6R,6aR)- and (3aS,4R,6S,6aR)-6-(2,6-dichloropurin-9-yl)-2,2-dimethyltetrahydrothieno[3,4-d][1,3]dioxol-4-yl methyl ester compound (17)

415 mg (2.2 mmol) of 2,6-dichloropurine and a catalytic amount of ammonium sulfate were suspended in 80 mL of anhydrous hexamethyldisilazane and stirred under reflux for 6 h. The reaction mixture was concentrated under reduced pressure and dry conditions, and the concentrate was dissolved in 15 mL of dichloroethane. 668 mg (1.9 mmol) of benzoic acid (3aS,4R,6R,6aR)- and (3aS,4R,6S,6aR)-6-acetoxy-2,2-dimethyltetrahydrothieno[3,4-d][1,3]dioxol-4-yl methyl ester dissolved in 20 mL of dichloroethane were added, followed by cooling to −10° C. After adding 0.42 mL (2.18 mmol) of trimethylsilyl trifluoromethanesulfonate, the reaction mixture was stirred at −10° C. for 20 min, and then stirred under reflux for 4 h. Saturated sodium bicarbonate solution was added and the mixture was stirred for 15 min and then extracted with dichloromethane. The extract was washed with saturated saline solution, dried, filtered, and concentrated under reduced pressure. The concentrate was purified by silica gel column chromatography using the eluant (hexane:ethyl acetate=2:1 by volume) to obtain 409 mg (yield: 44%) of benzoic acid (3aS,4R,6R,6aR)-6-(2,6-dichloropurin-9-yl)-2,2-dimethyltetrahydrothieno[3,4-d][1,3]dioxol-4-yl methyl ester and 102 mg (yield: 11%) of benzoic acid (3aS,4R,6S,6aR)-6-(2,6-dichloropurin-9-yl)-2,2-dimethyltetrahydrothieno[3,4-d][1,3]dioxol-4-yl methyl ester as white foam, respectively.

β-anomer (3aS,4R,6R,6aR)
¹H-NMR(CDCl₃) δ: 1.39 (s, 3H), 1.64 (s, 3H), 4.11 (dt, 1H), 4.57 (dd, 1H), 4.75 (dd, 1H), 5.19 (dd, 1H), 5.40 (dd, 1H), 6.10 (d, 1H), 7.37–7.97 (m, 5H), 8.38 (s, 1H)
UV (methanol): $\lambda_{max}$ 269 nm (pH 7)

α-anomer (3aS,4R,6S,6aR)
¹H-NMR(CDCl₃) δ: 1.37 (s, 3H), 1.64 (s, 3H), 4.08 (m, 1H), 4.51 (dd, 1H), 4.62 (dd, 1H), 5.01 (m, 1H), 5.11 (m, 1H), 6.50 (d, 1H), 7.37–7.99 (m, 5H), 8.87 (s, 1H)
UV (methanol): $\lambda_{max}$ 279 nm (pH 7).

Experimental Example 18

Synthesis of benzoic acid (3aS,4R,6R,6aR)-6-(2-chloro-6-(3-iodobenzylamino)purin-9-yl)-2,2-dimethyltetrahydrothieno[3,4-d][1,3]dioxol-4-yl methyl ester compound (18)

1.5 mL of ethanol were added to 254 mg (0.53 mmol) of benzoic acid (3aS,4R,6R,6aR)-6-(2,6-dichloropurin-9-yl)-2,2-dimethyltetrahydrothieno[3,4-d][1,3]dioxol-4-yl methyl ester compound from the aforementioned Experimental Example 17, 200 mg (0.68 mmol) of 3-iodobenzylamine hydrochloride, and 0.22 mL (1.53 mmol) of triethylamine, which was stirred at ambient temperature for 3 days. The reaction mixture was distilled under reduced pressure, and the concentrate was purified by silica gel column chromatography using the eluant (hexane:ethyl acetate=1:1) to obtain 322 mg (yield: 90%) of benzoic acid (3aS,4R,6R,6aR)-6-(2-chloro-6-(3-iodobenzylamino)purin-9-yl)-2,2-dimethyltetrahydrothieno[3,4-d][1,3]dioxol-4-yl methyl ester as white foam.

$^1$H-NMR(CDCl$_3$) δ: 1.37 (s, 3H), 1.63 (s, 3H), 4.11 (dt, 1H), 4.57 (dd, 1H), 4.76 (m, 3H), 5.22 (dd, 1H), 5.38 (dd, 1H), 6.01 (d, 1H), 6.28 (br, 1H), 7.04–8.00 (m, 9H), 8.02 (s, 1H)

UV (methanol): $\lambda_{max}$ 272 nm (pH 7).

Experimental Example 19

Synthesis of benzoic acid (3aS,4R,6S,6aR)-6-(2-chloro-6-(3-iodobenzylamino)purin-9-yl)-2,2-dimethyltetrahydrothieno[3,4-d][1,3]dioxol-4-yl methyl ester compound (19)

1.5 mL of ethanol were added to 80 mg (0.17 mmol) of benzoic acid (3aS,4R,6S,6aR)-6-(2,6-dichloropurin-9-yl)-2,2-dimethyltetrahydrothieno[3,4-d][1,3]dioxol-4-yl methyl ester, 60 mg (0.22 mmol) of 3-iodobenzylamine hydrochloride, and 0.07 mL (0.49 mmol) of triethylamine, which was stirred at ambient temperature for 3 days. The reaction mixture was distilled under reduced pressure, and the concentrate was purified by silica gel column chromatography using the eluant (hexane:ethyl acetate=1:1) to obtain 102 mg (yield: 90%) of benzoic acid (3aS,4R,6S,6aR)-6-(2-chloro-6-(3-iodobenzylamino)purin-9-yl)-2,2-dimethyltetrahydrothieno[3,4-d][1,3]dioxol-4-yl methyl ester as white foam.

$^1$H-NMR(CDCl$_3$) δ: 1.23 (s, 3H), 1.28 (s, 3H), 3.89 (t, 1H), 3.94 (dd, 1H), 4.08 (dd, 1H), 4.65 (d, 2H), 5.01 (m, 2H), 5.81 (d, 1H), 6.91–7.75 (m, 9H), 8.83 (s. 1H)

UV (methanol): $\lambda_{max}$ 282 nm (pH 7).

Experimental Example 20

Synthesis of (2R,3R, 4S,5R)-2-[2-chloro-6-(3-iodobenzylamino)purin-9-yl]-5-hydroxymethyltetrahydrothiophene-3,4-diol compound (20)

6 mL of 80% aqueous acetic acid solution were added to 122 mg (0.18 mmol) of (3aS,4R,6R, 6aR)-6-[2-chloro-6-(3-iodobenzylamino)purin-9-yl)]-2,2dimethyltetrahydrothieno[3,4-d][1,3]dioxol-4-yl methyl ester, which was then stirred at 55° C. for 12 h. The reaction mixture was distilled under reduced pressure, and then the pH of the concentrate was adjusted to neutral by adding saturated ammonia methanol solution. The concentrate was purified by silica gel column chromatography using the eluent (dichloromethane and methanol=15:1) to obtain (2R,3S,4R,5R)-5-[2-chloro-6-(3-iodobenzylamino)purin-9-yl]-3,4-dihydroxytetrahydrothiophen-2-yl methyl ester as a white foam. The aforementioned (2R,3S,4R,5R)-5-[2-chloro-6-(3-iodobenzylamino)purin-9-yl]-3,4-dihydroxytetrahydrothiophen-2-yl methyl ester was dissolved in 8 mL of methanol to which 30 mg (0.58 mmol) of sodium methoxide were added. The reaction mixture was stirred at ambient temperature for 4 h and the pH of the solution was adjusted to neutral with acetic acid, followed by distillation under reduced pressure. The concentrate was purified by silica gel column chromatography using the eluant (dichloromethane:methanol=6:1) to obtain 51 mg (yield: 53%) of (2R,3R,4S,5R)-2-[2-chloro-6-(3-iodobenzylamino)purin-9-yl]-5-hydroxymethyltetrahydrothiophene-3,4-diol a s white solids (see Table 3).

Melting point: 112–114° C.

$[\alpha]^{26}_D$: −28.3 (c 0.1, methanol)

$\nu_{MAX}$ (KBr)/cm$^{-1}$: 1316,1622, 3400

$^1$H-NMR (DMSO d$_8$) δ: 3.29 (m, 1H), 3.62 (m, 1H), 3.78 (m, 1H), 4.20 (d, 1H), 4.61 (m, 3H), 5.17 (t, 1H), 5.34 (d, 1H), 5.58 (d, 1H), 5.77 (d, 1H), 7.13 (t, 1H), 7.34 (d, 1H), 7.59 (d, 1H), 7.74 (s, 1H), 8.53 (s, 1H), 8.92 (br t, 1H)

$^{13}$C-NMR (DMSO-d$_6$) δ: 42.2, 53.1, 61.1, 62.8, 72.8, 76.7, 126.5, 130.2, 135.3, 135.7, 140.4

UV (methanol): $\lambda_{max}$ 273 nm (pH 7).

Experimental Example 21

Synthesis of (2S,3R, 4S,5R)-2-[2-chloro-6-(3-iodobenzylamino)purin-9-yl]-5-hydroxymethyltetrahydrothiophene-3,4-diol compound (21)

3 mL of 80% aqueous acetic acid solution were added to 50 mg (0.07 mmol) of (3aS,4R,6S,6aR)-6-[2-chloro-6-(3-iodobenzylamino)purin-9-yl)-2,2-dimethyltetrahydrothieno[3,4-d][1,3]dioxol-4-yl methyl ester, which was then stirred at 55° C. for 12 h. The reaction mixture was distilled under reduced pressure, and then the pH of the concentrate was adjusted to neutral by adding saturated ammonia methanol solution. The concentrate was purified by silica gel column chromatography using the eluant (dichloromethane and methanol=15:1) to obtain (2R,3S,4R,5S)-(5-[2-chloro-6-(3-iodobenzylamino)purin-9-yl]-3,4-dihydroxytetrahydrothiophen-2-yl methyl ester as white foam. The aforementioned (2R,3S,4R,5S)-(5-[2-chloro-6-(3-iodobenzylamino)purin-9-yl]-3,4-dihydroxytetrahydrothiophen-2-yl methyl ester was dissolved in 4 mL of methanol to which 15 mg (0.29 mmol) of sodium methoxide were added. The reaction mixture was stirred at ambient temperature for 4 h and the pH of the solution was adjusted to neutral with acetic acid, followed by distillation under reduced pressure. The concentrate was purified by silica gel column chromatography using the eluant (dichloromethane:methanol=6:1) to obtain 21 mg (yield: 54%) of (2S,3R,4S,5R)-2-[2-chloro-6-(3-iodobenylamino)purin-9-yl]$_5$-hydroxymethyltetrahydrothiophene-3,4-diol as white solids (see Table 2).

Melting point: 123–124° C.

$\nu_{max}$ (KBr)/cm$^{-1}$: 1557,1608, 3429

$^1$H-NMR (DMSO-d$_6$) δ: 3.43 (br d, 1H), 3.56 (dd, 1H), 3.71 (dd, 1H), 4.06 (dd, 1H), 4.27 (dd, 1H), 4.57 (dd, 1H), 4.69 (dd, 1H), 5.42 (d, 1H), 5.57 (t, 1H), 5.58 (d, 1H), 5.95 (d, 1H), 7.09 (t, 1h), 7.33 (d, 1H), 7.54 (d, 1H), 7.73 (s, 1H), 8.20 (br s, 1H), 8.59 (s, 1H)

UV (methanol): $\lambda_{max}$ 283 nm (pH 7).

TABLE 2

(IV)

| Compound group | Compound | R₁ | R₂ | R₃ | R'₃ | Spectral data |
|---|---|---|---|---|---|---|
| IV | 21 | 3-Iodo-benzyl | Chlorine | Hydrogen | Hydroxy-methyl | $^1$H-NMR(DMSO-d$_6$) δ: 3.43(br d, 1H), 3.56(dd, 1H), 3.71(dd, 1H), 4.06 (dd, 1H), 4.27(dd, 1H), 4.57(dd, 1H), 4.69(dd, 1H), 5.42(d, 1H), 5.57 (t, 1H), 5.58(d, 1H), 5.95(d, 1H), 7.09(t, 1H), 7.33(d, 1H), 7.54 (d, 1H), 7.73(s, 1H), 8.20(br s, 1H), 8.59(s, 1H) |

Experimental Example 22

Synthesis of benzoic acid (3aS,4R,6R,6aR)-6-[2-chloro-6-methylaminopurin-9-yl)-2,2-dimethyltetrahydrothieno-[3,4-d][1,3]dioxol-4-yl methyl ester compound (22)

454 mg (0.94 mmol) of benzoic acid (3aS,4R,6R,6aR)-6-[2,6-dichloropurin-9-yl)-2,2-dimethyltetrahydrothieno-[3,4-d][1,3]dioxol-4-yl methyl ester were dissolved in 20 mL (40 mmol) of 2N methylamine-tetrahydrofuran solution, which was stirred at ambient temperature in a sealed container for 24 h. The reaction mixture was concentrated under reduced pressure, and the concentrate was purified by silica gel column chromatography using the eluant (hexane:ethyl acetate=1:1) to obtain 383 mg (yield: 85%) benzoic acid (3aS,4R,6R,6aR)-6-[2-chloro-6-methylaminopurin-9-yl)-2,2-dimethyltetrahydrothieno-[3,4-d][1,3]dioxol-4-yl methyl ester as white foam.

$^1$H-NMR(CDCl$_3$) δ: 1.37 (s, 3H), 1.63 (s, 3H), 3.02 (d, 3H), 4.01 (dt, 1H), 4.57 (dd, 1H), 4.75 (dd, 1H), 5.23 (dd, 1H), 5.38 (dd, 1H), 6.01 (d, 1H), 6.28 (br s, 1H), 7.40–8.00 (m, 5H), 8.02 (s, 1H)

UV (methanol): λ$_{max}$ 271 nm (pH 7).

Experimental Example 23

Synthesis of (2R,3R,4S,5R)-2-(2-chloro-6-methylaminopurin-9-yl)-5-hydroxymethyltetrahydrothiophene-3,4-diol compound (23)

5 mL of 80% aqueous acetic acid solution were added to 105 mg (0.22 mmol) of benzoic acid (3aS,4R,6R,6aR)-6-(2-chloro-6-methylaminopurin-9-yl)-2,2-dimethyltetrahydrothieno[3,4-d][1,3]dioxol-4-yl methyl ester, which was then stirred at 55° C. for 12 h. The reaction mixture was distilled under reduced pressure, and then the pH of the concentrate was adjusted to neutral by adding a saturated ammonia methanol solution. The concentrate was purified by silica gel column chromatography using the eluant (dichloromethane and methanol=15:1) to obtain benzoic acid (2R,3S,4R,5R)-5-[2-chloro-6-methylaminopurin-9-yl]-3,4-dihydroxytetrahydrothiophen-2-yl methyl ester as white foam. The aforementioned (benzoic acid (2R,3S, 4R,5R)-5-[2-chloro-6-methylaminopurin-9-yl]-3,4-dihydroxytetrahydrothiophen-2-yl methyl ester was dissolved in 5 mL of methanol to which 15 mg (0.29 mmol) of sodium methoxide were added. The reaction mixture was stirred at ambient temperature for 4 h and the pH of the solution was adjusted to neutral with acetic acid, which was then distilled under reduced pressure. The concentrate was purified by silica gel column chromatography using the eluant (dichloromethane:methanol=6:1) to obtain 38 mg (yield: 52%) of ((2R,3R,4S,5R)-2-(2-chloro-6-methylaminopurin-9-yl)$_5$-hydroxymethyltetrahydrothiophene-3,4-diol as white solids (see Table 3).

Melting point: 239–241° C.

[α]$^{24}_D$: −30.6 (c 0.1 methanol)

ν$_{max}$ (KBr)/cm$^{-1}$: 1312, 1626, 3419

$^1$H-NMR (DMSO-d$_6$) δ: 2.92 (d, 3H), 3.30 (br s, 1H), 3.62 (m, 1H), 3.79 (m, 1H), 4.20 (dd, 1H), 4.61 (m, 1H), 5.16 (t, 1H), 5.34 (d, 1H), 5.58 (d, 1H), 5.77 (d, 1H), 8.26 (br s, 1H), 8.47 (s, 1H)

$^{13}$C-NMR (DMSO-d$_6$) δ: 27.5, 53.7, 63.5, 73.5, 77.4, 118.9, 140.5, 150.0, 153.6, 155.9

UV (methanol): λ$_{max}$ 271 nm (pH 7).

Experimental Example 24

Synthesis of benzoic acid (3aS,4R,6R,6aR)-6-[6-amino-2-chloro-purin-9-yl)-2,2-dimethyltetrahydrothieno-[3,4-d][1,3]dioxol-4-yl methyl ester compound (24)

454 mg (0.94 mmol) of benzoic acid (3aS,4R,6R,6aR)-6-[2,6-dichloropurin-9-yl)-2,2-dimethyltetrahydrothieno-[3,4-d][1,3]dioxol-4-yl methyl ester were dissolved in 25 mL of saturated ammonia ethanol solution, which was transferred into a sealed container and heated at 50° C. for 12 h. The reaction mixture was concentrated under reduced pressure, and the concentrate was purified by silica gel column chromatography using the eluant (hexane:ethyl acetate=1:1) to obtain 384 mg (yield: 88%) benzoic acid (3aS,4R,6R, 6aR) 6-[6-amino-2-chloro-purin-9-yl)-2,2-dimethyltetrahydrothieno-[3,4-d][1,3]dioxol-4-yl methyl ester as a white foam.

¹H-NMR(CDCl₃) δ: 1.37 (s, 3H), 1.63 (s, 3H), 4.01 (dt, 1H), 4.57 (dd, 1H), 4.77 (dd, 1H), 5.23 (dd, 1H), 5.38 (dd, 1H), 6.02 (d, 1H), 6.29 (br s, 2H), 7.40–8.00 (m, 5H), 8.02 (s, 1H)

UV (methanol): $\lambda_{max}$ 264 nm (pH 7).

Experimental Example 25

Synthesis of (2R,3R,4S,5R)-2-(2-chloro-6-aminopurin-9-yl)-5-hydroxymethyltetrahygrothiophene-3,4-diol compound (25).

5 mL of 80% aqueous acetic acid solution were added to 102 mg (0.22 mmol) of benzoic acid (3aS,4R,6R,6aR)-6-(6-amino-2-chloro-purin-9-yl)-2,2-dimethyltetrahydrothieno[3,4-d][1,3]dioxol-4-yl methyl ester, which was then stirred at 55° C. for 12 h. The reaction mixture was distilled under reduced pressure, and then the pH of the concentrate was adjusted to neutral by adding saturated ammonia methanol solution. The concentrate was purified by silica gel column chromatography using the eluant (dichloromethane and methanol=15:1) to obtain benzoic acid (2R,3S,4R,5R)-5-[6-amino-2-chloro-purin-9-yl]-3,4-dihydroxytetrahydrothiophen-4-yl methyl ester as white foam. The aforementioned benzoic acid (2R,3S,4R,5R)-5-[6-amino-2-chloro-purin-9-yl]-3,4-dihydroxytetrahydrothiophen-4-yl methyl ester was dissolved in 5 mL of methanol to which 15 mg (0.29 mmol) of sodium methoxide were added. The reaction mixture was stirred at ambient temperature for 4 h and the pH of the solution was adjusted to neutral with acetic acid, followed by distillation under reduced pressure. The concentrate was purified by silica gel column chromatography using the eluant (dichloromethane:methanol=6:1) to obtain 37 mg (yield: 53%) of (2R,3R,4S,5R)-2-(2-chloro-6-aminopurin-9-yl)-5-hydroxymethyltetrahydrothiophene-3,4-diol as white solids (see Table 3).

Melting point: 220–222° C.

$[\alpha]^{24}_D$: –24.6 (c 0.7 methanol)

$\nu_{MAX}$ (KBr)/cm⁻¹: 1204,1647,3420

¹H-NMR (DMSO-d₆) δ: 3.30 (br s, 1H), 3.62 (m, 1H), 3.79 (m, 1H), 4.20 (dd, 1H), 4.61 (dd, 1H), 5.16 (t, 1H), 5.34 (d, 1H), 5.58 (d, 1H), 5.77 (d, 1H), 7.81 (br s, 2H), 8.48 (s, 1H)

¹³C-NMR (DMSO-d₆) δ: 53.3, 61.2, 63.1, 73.1, 76.9, 118.0, 140.4, 150.7, 152.9, 156.7

UV (methanol): $\lambda_{max}$ 264 nm (pH 7).

Experimental Example 26

Synthesis of benzoic acid (2R,3S,4R,5R)-5-(6-amino-2-chloro-purin-9-yl)-3,4-dihydroxytetrahydrothiophen-4-yl methyl ester compound (26)

5 mL of 80% aqueous acetic acid solution were added to 102 mg (0.22 mmol) of benzoic acid (3aS,4R,6R,6aR)-6-(6-amino-2-chloro-purin-9-yl)-2,2-dimethyltetrahydrothieno[3,4-d][1,3]dioxol-4-yl methyl ester, which was then stirred at 55° C. for 12 h. The reaction mixture was distilled under reduced pressure, and the pH of the concentrate was adjusted to neutral by adding saturated ammonia methanol solution. The concentrate was purified by silica gel column chromatography using the eluant (dichloromethane and methanol=15:1) to obtain 63 mg (yield: 68%) of benzoic acid (2R,3S,4R,5R)-5-[6-amino-2-chloro-purin-9-yl]-3,4-dihydroxytetrahydrothiophen-4-yl methyl ester as white foam.

Experimental Example 27

Synthesis of (2R,3S,4R,5R)-[5-(6-amino-2-chloro-purin-9-yl]-3,4-bis(tert-butyldimethylsilanyloxy)tetrahydrothiophen-2-yl]-methanol compound (27)

230 mg (0.55 mmol) of benzoic acid (2R,3S,4R,5R)-5-[6-amino-2-chloro-purin-9-yl]-3,4-dihydroxytetrahydrothiophen-4-yl methyl ester from the aforementioned Experimental Example 26, 225 mg (3.30 mmol) of imidazole, and 249 mg (1.65 mmol) of tert-butylchlorodimethylsilane were dissolved in 10 mL of N,N-dimethylformamide, which was stirred at 50° C. for 24 h. Water was added to the reaction mixture, and the compound was extracted with dichloromethane. The organic layer was washed sequentially with water, saturated sodium bicarbonate solution, and saturated saline solution, then dried, filtered, and distilled under reduced pressure. Without further purification, the concentrate was dissolved in 8 mL of methanol to which 45 mg (0.83 mmol) of sodium methoxide were added. The reaction mixture was stirred at ambient temperature for 4 h, then neutralized with acetic acid and distilled under reduced pressure. The concentrate was purified by silica gel column chromatography using the eluant (hexane:ethyl acetate=2:1) to obtain 169 mg (yield: 56%) of (2R,3 S,4R,5R)-[5-(6-amino-2-chloro-purin-9-yl)-3,4-bis(tert-butyldimethylsilanyloxy)tetrahydrothiophen-2-yl]-methanol as white foam.

¹H-NMR(CDCl₃) δ: 1.01 (m, 12H), 0.79 (s, 9H), 0.83 (s, 9H), 3.41 (dd, 1H), 4.21 (m, 1H), 4.56 (dd, 1H), 4.73 (m, 1H), 4.86 (dd, 1H), 5.71 (d, 1H), 6.20 (br s, 1H), 7.61 (br s, 2H), 8.12 (s, 1H)

UV (methanol): $\lambda_{max}$ 263 nm (pH 7)

Experimental Example 28

Synthesis of (2S,3S,4R,5R)-[5-(6-amino-2-chloro-purin-9-yl)-3,4-bis(tert-butyldimethylsilanyloxy)tetrahydrothiophene-2-carboxylic acid methyl amide compound (28)

150 mg (0.27 mmol) of (2R,3S,4R,5R)-[5-(6-amino-2-chloro-purin-9-yl)-3,4-bis(tert-butyldimethylsilanyloxy)tetrahydrothiophen-2-yl]-methanol from the aforementioned Experimental Example 27 were dissolved in 20 mL of anhydrous N,N-dimethylformamide to which 2.34 g (6.21 mmol) of pyridinium dichromate were added. The reaction mixture was stirred at ambient temperature for 20 h. Water was added to the reaction mixture, which was then extracted with ethyl acetate several times. The organic layer was dried and filtered. The filtrate was distilled under reduced pressure to obtain the concentrate, an acid derivative. Without further purification, the concentrate was dissolved in 6 mL of acetone to which 1.0 mL (10.57 mmol) of dimethyl sulfate and 100 mg (0.72 mmol) of potassium carbonate were added, followed by stirring at ambient temperature for 2 h. The reaction mixture was distilled under reduced pressure, and the obtained concentrate was dissolved in ethyl acetate, which was washed with water and saturated saline solution. The organic layer was distilled under reduced pressure to obtain the methyl ester derivative as a foam. Without further purification, 20 mL (40 mmol) of 2N methylamine tetrahydrofuran solution were added to the aforementioned methyl ester derivative, which was stirred in a sealed container at 50° C. for 24 h. After the reaction mixture was distilled under reduced pressure, the obtained concentrate was purified by silica gel column chromatography using the eluant (hexane:ethyl acetate=1:1) to obtain 80 mg (yield: 51%) of (2S,3S,4R,5R-[5-(6-amino-2-chloro-purin-9-yl)-3,4-bis(tert-butyldimethylsilanyloxy)tetrahydrothiophene-2-carboxylic acid methyl amide as white foam.

$^1$H-NMR(CDCl$_3$) δ: 0.01 (m, 12H), 0.79 (s, 9H), 0.85 (s, 9H), 2.67 (d, 3H), 3.78 (d, 1H), 4.35 (m, 1H), 4.57 (m, 1H), 5.70 (d, 1H), 7.72 (br s, 2H), 7.72 (br s, 1H), 8.10 (s, 1H)

UV (methanol): $λ_{max}$ 264 nm (pH 7)

Experimental Example 29

Synthesis of (2S,3S,4R,5R)-[5-(6-amino-2-chloro-purin-9-yl)-3,4-dihydroxytetrahydrothiophene-2-carboxylic acid methyl amide compound (29)

140 mg (0.24 mmol) of (2S,3S,4R,5R)-[5-(6-amino-2-chloro-purin-9-yl)-3,4-bis(tert-butyldimethylsilanyloxy)tetrahydrothiophen-2-yl]-methyl amide from the aforementioned Experimental Example 28 were dissolved in 10 mL of anhydrous tetrahydrofuran to which 0.67 mL (0.67 mmol, 1M tetrahydrofuran solution) of tetrabutylammonium fluoride was added. The reaction mixture was stirred at ambient temperature for 1 h. The reaction mixture was distilled under reduced pressure and the concentrate was purified by silica gel column chromatography using the eluant (dichloromethane:methanol=4:1) to obtain 58 mg (yield: 69%) of (2S,3S,4R,5R)-5-(6-amino-2-chloro-purin-9-yl)-3,4-dihydroxytetrahydrothiophene-2-carboxylic acid methyl amide as white solids (see Table 3).

Melting point: 233–235° C.

$[α]^{26}_D$: −20.2 (c 0.1 methanol)

$^1$H-NMR (DMSO-d$_6$) δ: 2.70 (d, 3H), 3.82 (d, 1H), 4.36 (dd, 1H), 4.53 (m, 1H), 5.60 (d, 1H), 5.78 (d, 1H), 5.82 (d, 1H), 7.87 (br s, 2H), 8.33 (br d, 1H), 8.55 (s, 1H)

$^{13}$C-NMR (DMSO-d$_6$) δ: 51.8, 57.5, 62.5, 75.4, 78.1, 118.4, 140.1, 150.5, 153.0, 156.7, 170.7

UV (methanol): $λ_{max}$ 264 nm (pH 7)

Experimental Example 30

Synthesis of benzoic acid (2R,3S,4R,5R)-5-(2-chloro-6-methylaminopurin-9-yl)-3,4-dihydroxytetrahydrothiophen-2-yl methyl ester compound (30)

5 mL of 80% aqueous acetic acid solution were added to 105 mg (0.22 mmol) of benzoic acid (3aS,4R,6R,6aR)-6-(2-chloro-6-methylaminopurin-9-yl)-2,2-dimethyltetrahydrothieno[3,4-d][1,3]dioxol-4-yl methyl ester, which was then stirred at 55° C. for 12 h. The reaction mixture was distilled under reduced pressure, then neutralized by adding saturated ammonia methanol solution. The concentrate was purified by silica gel column chromatography using the eluant (dichloromethane and methanol=15:1) to obtain 93 mg (yield: 68%) of benzoic acid (2R,3S,4R,5R)-5-[2-chloro-6-methylaminopurin-9-yl]-3,4-dihydroxytetrahydrothiophen-2-yl methyl ester as white foam.

Experimental Example 31

Synthesis of (2R,3S,4R,5R)-[3,4-bis(tert-butyldimethylsilanyloxy)-5-(2-chloro-6-methylaminopurin-9-yl)-tetrahydrothiophen-2-yl]-methanol compound (31)

160 mg (0.38 mmol) of benzoic acid (2R,3S, 4R,5R)-5-[2-chloro-6-methylaminopurin-9-yl]-3,4-dihydroxytetrahydrothiophen-2-yl methyl ester from the aforementioned Experimental Example 30, 155 mg (2.28 mmol) of imidazole, and 172 mg (1.14 mmol) of tert-butylchlorodimethylsilane were dissolved in 10 mL of N,N-dimethylformamide, which was stirred at 50° C. for 24 h. Water was added to the reaction mixture, and the compound was extracted with dichloromethane. The organic layer was washed sequentially with water, saturated sodium bicarbonate solution, and saturated saline solution, then dried, filtered, and distilled under reduced pressure. Without further purification, the concentrate was dissolved in 8 mL of methanol to which 45 mg (0.83 mmol) of sodium methoxide were added. The reaction mixture was stirred at ambient temperature for 4 h, then neutralized with acetic acid and distilled under reduced pressure. The concentrate was purified by silica gel column chromatography using the eluant (hexane:ethyl acetate=2:1) to obtain 112 mg (yield: 53%) of (2R,3S,4R,5R)-[3,4-bis(tert-butyldimethylsilanyloxy)-5-(2-chloro-6-methylaminopurin-9-yl)tetrahydrothiophen-2-yl]-methanol as white foam.

$^1$H-NMR(CDCl$_3$) δ: 0.01 (m, 12H), 0.81 (s, 9H), 0.86 (s, 9H), 3.13 (br s, 3H), 3.72 (dd, 1H), 4.24 (m, 1H), 4.48 (dd, 1H), 4.75 (m, 1H), 4.87 (dd, 1H), 5.67 (d, 1H), 5.88 (br s, 1H), 8.00 (s, 1H), 8.03 (br s, 1H)

UV (methanol): $λ_{max}$ 269 nm (pH 7)

Experimental Example 32

Synthesis of (2S,3S,4R,5R)-3,4-bis(tert-butyldimethylsilanyloxy)-5-(2-chloro-6-methylaminopurin-9-yl)tetrahydrothiophene-2-carboxylic acid methyl amide compound (32)

105 mg (0.19 mmol) of (2R,3S,4R,5R)-[3,4-bis(tert-butyldimethylsilanyloxy)-5-(2-chloro-6-methylaminopurin-9-yl)-tetrahydrothiophen-2-yl]-methanol from the aforementioned Experimental Example 31 were dissolved in 15 mL of anhydrous N,N-dimethylformamide to which 1.64 g (4.36 mmol) of pyridinium dichromate were added. The reaction mixture was stirred at ambient temperature for 20 h. Water was added to the reaction mixture, which was extracted with ethyl acetate several times. The organic layer was dried and filtered. The filtrate was distilled under reduced pressure to obtain the concentrate, an acid derivative. Without further purification, the concentrate was dissolved in 4 mL of acetone to which 1.0 mL (10.57 mmol) of dimethyl sulfate and 80 mg (10.58 mmol) of potassium carbonate were added, followed by stirring at ambient temperature for 2 h. The reaction mixture was distilled under reduced pressure, and the obtained concentrate was dissolved in ethyl acetate, then washed with water and saturated saline solution. The organic layer was distilled under reduced pressure to obtain the methyl ester derivative as foam. Without further purification, 15 mL (30 mmol) of 2N methylamine tetrahydrofuran solution were added to the aforementioned methyl ester derivative, then it was stirred in a sealed container at 50° C. for 24 h. After the reaction mixture was distilled under reduced pressure, the obtained concentrate was purified by silica gel column chromatography using the eluant (hexane: ethyl acetate=1:1) to obtain 48 mg (yield: 44%) of (2S,3S, 4R,5R)-3,4-bis(tert-butyldimethylsilanyloxy)-5-(2-chloro-6-methylaminopurin-9-yl)tetrahydrothiophene-2-carboxylic acid methyl amide as white foam.

$^1$H-NMR(CDCl$_3$) δ: 0.01 (s, 12H), 0.82 (s, 9H), 0.85 (s, 9H), 3.21 (br s, 3H), 3.21 (br s, 3H), 3.75 (d, 1H), 4.28 (m, 1H), 4.65 (m, 1H), 5.77 (d, 1H), 7.12 (br s, 1H), 8.03 (br s, 1H), 8.44 (s, 1H)

UV (methanol): λ$_{max}$ 270 nm (pH 7)

Experimental Example 33

Synthesis of (2S,3S,4R,5R)-5-(2-chloro-6-methylaminopurin-9-yl)-3,4-dihydroxytetrahydrothiophene-2-carboxylic acid methyl amide compound (33)

48 mg (0.08 mmol) of (2S,3S,4R,5R)-3,4-bis(tert-butyldimethylsilanyloxy)-5-(2-chloro-6-methylaminopurin-9-yl)-tetrahydrothiophene-2-carboxylic acid methyl amide were dissolved in anhydrous tetrahydrofuran to which 0.22 mL (0.22 mmol, 1M tetrahydrofuran solution) of tetrabutylammonium fluoride was added. The reaction mixture was stirred at ambient temperature for 1 h. The reaction mixture was distilled under reduced pressure and the concentrate was purified by silica gel column chromatography using the eluant (dichloromethane:methanol=6:1) to obtain 19 mg (yield: 65%) of (2S,3S,4R,5R)-5-(2-chloro-6-methylaminopurin-9-yl-3,4-dihydroxytetrahydrothiophene-2-carboxylic acid methyl amide as white solids (see Table 3).

Melting point: 130–141° C.

[α]$^{19}_D$: −22.0 (c 0.13 methanol)

$^1$H-NMR (DMSO-d$_6$) δ:2.69 (d, 3H), 2.92 (d, 3H), 3.81 (d, 1H), 4.36 (dd, 1H), 4.52 (dd, 1H), 5.16 (d, 1H), 5.78 (d, 1H), 5.82 (d, 1H), 7.23 (br s, 1H), 8.33 (br d, 2H), 8.54 (s, 1H)

$^{13}$C-NMR (DMSO-d$_6$) o: 51.8, 55.5, 62.6, 69.6, 75.4, 78.2, 118.5, 139.9, 149.5, 153.3, 155.5, 170.7

UV (methanol): λ$_{max}$ 270 nm (pH 7)

Exierimental Example 34

Synthesis of (2R,3S, 4R,5R)-{3,4-bis(tert-butyldimethylsilanyloxy)-5-[2-chloro-6-(3-iodobenylamino) purin-9-yl]-tetrahydrothiophen-2-yl}methanol compound (34)

6 mL of 80% aqueous acetic acid solution were added to 122 mg (0.18 mmol) of benzoic acid (3aS,4R,6R,6aR)-6-(2-chloro-6-(3-iodobenzylamino)purin-9-yl)-2,2-dimethyltetrahydrothieno[3,4d])[1,3]dioxol-4-yl methyl ester, which was then stirred at 55° C. for 12 h. The reaction mixture was distilled under reduced pressure, then adjusted to neutral by adding saturated ammonia methanol solution. The concentrate was purified by silica gel column chromatography using the eluant (dichloromethane and methanol=15:1) to obtain benzoic acid (2R,3S,4R,5R)-5-[2-chloro-6-(iodobenzylamino)purin-9-yl]-3,4-dihydroxytetrahydrothiophen-2-yl methyl ester as white foam. 450 mg (0.71 mmol) of benzoic acid (2R,3S, 4R,5R)-5-[2-chloro-6-(iodobenzyyamino)purin-9-yl]-3,4-dihydroxytetrahydrothiopher-2-yl methyl ester obtained above, 286 mg (4.20 mmol) of imidazole, and 316 mg (2.10 mmol) of tert-butylchlorodimethylsilane were dissolved in 20 mL of anhydrous N,N-dimethylformamide, which was then stirred at 50° C. for 24 h. Water was added to the reaction mixture, which was extracted with dichloromethane. The organic layer was washed sequentially with water, saturated sodium bicarbonate solution, and then saturated saline solution. The organic layer was dried and then distilled under reduced pressure. Without further purification, the concentrate was dissolved in 15 mL of methanol to which 90 mg (1.74 mmol) of sodium methoxide were added. The reaction mixture was stirred at ambient temperature for 4 h and the solution was neutralized with acetic acid, then distilled under reduced pressure. The concentrate was purified by silica gel column chromatography using the eluant (hexane:ethyl acetate=2:1) to obtain 290 mg (yield: 54%) of (2R,3S,4R,5R){3,4-bis(tert-butyldimethylsilanyloxy)5-[2-chloro-6-(3-iodobenzylamino)purin-9-yl]-tetrahydrothiophen-2-yl}methanol as white solids.

$^1$H-NMR(CDCl$_3$) δ: 0.01 (m, 12H), 0.80 (s, 9H), 0.85 (s, 9H), 3.29 (dd, 1H), 4.24 (m, 1H), 4.47 (dd, 1H), 4.73 (m, 3H), 4.86 (dd, 1H), 5.67 (d, 1H), 6.15 (br s, 1H), 7.02 (t, 1H), 7.27 (d, 1H), 7.43 (d, 1H), 7.59 (br s, 1H), 7.67 (s, 1H), 80.3 (s, 1H)

UV (methanol): λ$_{max}$ 272 nm (pH 7)

Experimental Example 35

Synthesis of (2S,3S,4R,5R)-3,4-bis(tert-butyldimethylsilanyloxy)-5-[2-chloro-6-(3-iodobenzylamino) purin-9-yl]-tetrahydrothiophene-2-carboxylic acid methyl amide compound (35)

228 mg (0.30 mmol) of (2R,3S,4R,5R)-[3,4-bis(tert-butyldimethylsilanyloxy)-5-(2-chloro-6-(3-iodobenzylamino) purin-9-yl)-tetrahydrothiophen-2-yl]-methanol were dissolved in 20 mL of anhydrous N,N-dimethylformamide to which 2.6 g (7.0 mmol) of pyridinium dichromate were added. The reaction mixture was stirred at ambient temperature for 20 h. Water was added to the reaction mixture, which was then extracted with ethyl acetate several times. The organic layer was dried and filtered. The filtrate was distilled under reduced pressure to obtain the concentrate, an acid derivative. Without further purification, the concentrate was dissolved in 6 mL of acetone to which 1.0 mL (10.57 mmol) of dimethyl sulfate and 100 mg (0.72 mmol) of potassium carbonate were added, followed by stirring at ambient temperature for 2 h. The reaction mixture was distilled under reduced pressure, and the obtained concentrate was dissolved in ethyl acetate, then washed with water and saturated saline solution. The organic layer was distilled under reduced pressure to obtain the methyl ester derivative as foam. Without further purification, 20 mL (40 mmol) of 2N methylamine tetrahydrofuran solution were added to the aforementioned methyl ester derivative, then it was stirrred in a sealed container at 50° C. for 24 h. After the reaction mixture was distilled under reduced pressure, the obtained concentrate was purified by silica gel column chromatography using the eluent (hexane:ethyl acetate=1:2) to obtain 99 mg (yield: 42%) of (2S,3S,4R,5R)-3,4-bis(tert-butyldimethylsilanyloxy)-5-(2-chloro-6-(3-iodobenzylaminopurin-9-yl)-tetrahydrothiophene-2-carboxylic acid methyl amide as white foam.

$^1$H-NMR(CDCl$_3$) δ: 0.01 (m, 12H), 0.70 (s, 9H), 0.84 (s, 9H), 2.70 (d, 3H), 3.81 (d, 1H), 4.39 (m, 1H), 4.55 (m, 1H), 4.61 (d, 2H), 5.83 (d, 1H), 7.15 (t, 1H), 7.36 (d, 1H), 7.61 (d, 1H), 7.76 (s, 1H), 8.33 (br s, 1H), 8.61 (d, 1H) 9.00 (br s, 1H)

UV (methanol): λ$_{max}$ 272 nm (pH 7)

Experimental Example 36

Synthesis of (2S,3S,4R,5R)[5-(2-chloro-6-(3-iodo-benzylamino)purin-9-yl)-3,4-dihydroxytetrahydrothiophene-2-carboxylic acid methyl amide compound (36)

75 mg (0.09 mmol) of (2S,3S,4R,5R)-3,4-bis(tert-butyldimethylsilanyloxy)-5-[2-chloro-6-(3-iodobenzylamino) purin-9-yl]-tetrahydrothiophene-2-carboxylic acid methyl amide from the aforementioned Experimental Example 35 were dissolved in 5 mL of anhydrous tetrahydrofuran to which 0.25 mL (0.25 mmol, 1 mol tetrahydrofuran solution) of tetrabutylammonium fluoride was added. The reaction mixture was stirred at ambient temperature for 1 h. The reaction mixture was distilled under reduced pressure and the concentrate was purified by silica gel column chromatography using the eluant (dichloromethane:methanol=7:1) to obtain 33 mg (yield: 63%) of (2S,3S,4R,5R)-5-[2-chloro-6-(3-iodobenzylamino)purin-9-yl]-3,4-dihydroxytetrahydrothiophene-2-carboxylic acid methyl amide as white solids (see Table 3).

Melting point: 140–141° C.
$[\alpha]^5_D$: −19.5 (c 0.32 methanol)
$^1$H-NMR (DMSO-$d_6$) δ: 2.69 (d, 3H), 3.82 (d 1H), 4.37 (dd, 1H), 4.55 (m, 1H), 4.60 (d, 2H), 5.59 (d, 1H), 5.78 (d, 1H), 5.83 (d, 1H), 7.13 (t, 1H), 7.35 (d, 1H), 7.60 (d, 1H), 7.75 (s, 1H), 8.32 br d, 1H), 8.60 (s, 1H), 8.99 (br t, 1H)
$^{13}$C-NMR (DMSO-$d_6$) δ: 42.5, 51.8, 59.7, 62.6, 75.4, 78.2, 118.4, 126.8, 130.5, 135.5, 136.0, 140.3, 141.8, 149.9, 153.0, 154.7, 170.3, 170.7,
UV (methanol):

Test Example 1

Binding Affinity Test of 4-thioadenosine Derivative Compound

Cell Culture and Receptor Binding

Chinese hamster ovary (CHO, ATCC; US Cell Strain Bank No. CCL-61) cells that express the $A_3$ receptor were cultured at 37° C. in the presence of 5% carbon dioxide in F-12 culture medium (Gibco Company, USA) containing 10% fetal bovine serum (FBS) and penicillin/streptomycin (100 U/mL and 100 μg/mL), and used.

The binding affinity for the CHO cell membrane [$^{125}$I]-4-amino-3-iodobenzyl]adenosine-5'-N-methyluronamide ([$^{125}$I]AB-MECA) was measured in a test tube holding 50/10/1 buffer solution which contains 50 μL of [$^{125}$I]AB-MECA, 100 μL of membrane suspended particle, and 50 μL of inhibitor. The inhibitor is first dissolved in dimethyl sulfoxide and diluted with buffer solution. The final concentration of DMSO should not exceed 1%. After culturing at 37° C. for 1 h, it was quickly filtered using a cell collector (TOMTEC Company, USA) and a GF/B filter (Whatman Company, USA). The test tube was rinsed three times with 3 mL of buffer solution, and the radioactivity was measured using a γ-counter. Nonspecific binding was determined in the presence of 40 μM of R-PIA and the equilibrium constant, $K_i$, was determined using the Cheng-Prusoff equation under the assumption that the $k_d$ value of [$^{125}$I]AB-MECA is 1.48 nM.-

TABLE 3

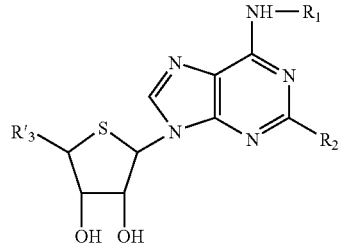

(III)

| Compound group | Compound | $R_1$ | $R_2$ | $R_3$ | $R'_3$ | Spectral data |
|---|---|---|---|---|---|---|
| III | 20 | 3-iodobenzyl | Chlorine | Hydrogen | Hydroxymethyl | $^1$H-NMR(DMSO-$d_6$)δ: 3.29(m, 1H), 3.62(m, 1H), 3.78(m, 1H), 4.20(d, 1H), 4.61(m, 3H), 5.34(d, 1H), 5.58(d, 1H), 5.77(d, 1H), 7.13(t, 1H), 7.34(d, 1H), 7.59(d, 1H), 7.74(s, 1H), 8.53(s, 1H) 8.92(br t, 1H) |
| | 23 | Methyl | Chlorine | Hydrogen | Hydroxymethyl | $^1$H-NMR(DMSO-$d_6$)δ: 2.92(d, 3H), 3.30(brs, 1H), 3.62(m, 1H), 3.79(m, 1H), 4.20(dd, 1H), 4.61(m, 1H), 5.16(t, 1H), 5.34(d, 1H), 5.58(d, 1H), 5.77(d, 1H), 8.26(br s, 1H), 8.47(s, 1H) |
| | 25 | Hydrogen | Chlorine | Hydrogen | Hydroxymethyl | $^1$H-NMR(DMSO-$d_6$)δ: 3.30(br s, 1H), 3.62(m, 1H), 3.79(m, 1H), 4.20(dd, 1H), 4.61(dd, 1H), 5.16(t, 1H), 5.34(d, 1H), 5.58(d, 1H), 5.77(d, 1H), 7.81(br s, 2H), 8.48(s, 1H) |
| III | 29 | Hydrogen | Chlorine | Hydrogen | Methylaminocarbonyl | $^1$H-NMR(DMSO-$d_6$)δ: 2.70(d, 3H), 3.82(d, 1H), 4.36(dd, 1H), 4.53(m, 1H), 5.60(d, 1H), 5.78(d, 1H), 5.82(d, 1H), 7.87(br s, 2H), 8.33(br d, 1H), 8.55(s, 1H) |
| | 33 | Methyl | Chlorine | Hydrogen | Methylaminocarbonyl | $^1$H-NMR(DMSO-$d_6$)δ: 2.69(d, 3H), 2.92(d, 3H), 3.81(d, 1H), 4.36(dd, 1H), 4.52(dd, 1H), 5.61(d, 1H), 5.78(d, 1H), 5.82(d, 1H), 7.23(brs, 1H), 8.33(br d, 2H), 8.54(s, 1H) |
| | 36 | 3-iodobenzyl | Chlorine | Hydrogen | Methylaminocarbonyl | $^1$H-NMR(DMSO-$d_6$)δ: 2.69(d, 3H), 3.82(d, 1H), 4.37(dd, 1H), 4.55(m, 1H), 4.60(d, 2H), 5.59(d, 1H), 5.78(d, 1H), 5.83(d, 1H), 7.13(t, 1H), 7.35(d, 1H), 7.60(d, 1H), 7.75(s, 1H), 8.32 (br d, 1H), 8.60(s, 1H), 8.99(br t, 1H) |

The binding of [³H]PIA ((R)-N⁶-(phenylisopropyl) adenosine) to $A_1$ and the binding of [³H]CGS21680(2-[[[4-(2–Carboxyethyl-phenyl)ethylamino]-5'-N-thylcarbamoyl) adenosine) to $A_{2a}$ were measured as described below. Adenosine deaminase was added while the membrane was cultured at 30° C. for 30 min with the radioactive ligand. The $IC_{50}$ values of each compound were determined for at least 6 different concentrations. This value was used to determine the $K_i$ value using the Plat program, wherein the Cheng-Prusoff equation was used under the assumption that the $K_d$ values of [³H]PIA and [³H]CGS 21680 are 1.0 and 14 nM, respectively.

Among the known adenosine derivatives, CL-IB-MECA used as a control group herein is known to exhibit outstanding agonist activity against $A_3$ among $A_1$, $A_2$, and $A_3$, but very low affinity toward $A_1$ and $A_2$ (Hea O. Kim, et al.; J. Med. Chem., 37(21), pp. 364–3621, 1994).

The test results showed that, among new thionucleoside compounds of the present invention, $K_i$ toward adenosine $A_3$ receptor of the compounds having the general formula (III) was in the range of 0.28–4.9 nM, indicating strong agonist activity compared to the existing human $A_3$ receptors. $K_i$ of the compound having the general formula (II) was found to be 4.3–8.0 nM, which means excellent antagonist activity. The compound having general formula (II) showed much lower affinity toward $A_1$ and $A_2$ than the existing compounds. Especially, compound 33 exhibited the most strong and selective $A_3$ agonist activity among the known compounds. The compounds showed excellent selectivity toward adenosine $A_3$ receptors.

Test Example 2

Toxicity Test

Animal studies were carried out to test the toxicity of the compounds pared in the present invention.

25±5 g ICR family mice (Joongang Study Animal) and 235±10 g specific pathogen free (SPF) Sprague Dawley rats (Joongang Study Animal) were divided into 3 groups. After 20 mg/kg, 10 mg/kg, and 1 mg/kg dose of compound 33 of the present invention were peritoneally administered, the toxicity was observed for 24 h.

In the test results, no deaths were observed in any of three groups, and there were no other observable symptoms related to weight increase or feed intake, etc., that were different from the control group. Therefore, it was confirmed that the thionucleoside derivative compounds are safe drugs.

The thionucleoside derivative compounds of the present invention may be administered in the following formulations. The following formulation examples are listed only to illustrate the present invention. The content of the present invention is not limited to these examples.

Formulation Example 1

Powder Formulation

| | |
|---|---|
| Dry powder compound 33 | 500 mg |
| Cornstarch | 100 mg |

TABLE 4

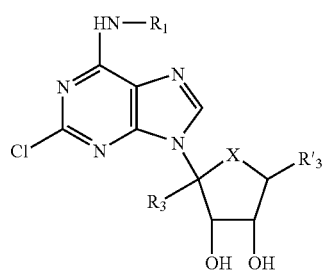

(V)

| Compound | | | | | $K_i$ (nM) or % Displacement | | | | |
|---|---|---|---|---|---|---|---|---|---|
| Compound | group | $R_1$ | $R_2$ | $R'_3$ | $hA_1$ | $rA_1$ | $hA_{2a}$ | $rA_{2a}$ | $hA_3$ |
| CL-IB-MECA | | 3-iodobenzyl | Hydrogen | CONHMe | 1240 ± 320 | 820 ± 570 | 5360 ± 2470 | 470 ± 365 | 1.0 ± 0.2 |
| 20 | III | 3-iodobenzyl | Hydrogen | $CH_2OH$ | 127 ± 35 | | | 285 ± 108 | 3.2 ± 0.98 |
| 25 | III | Hydrogen | Hydrogen | $CH_2OH$ | 238 ± 107 | | | 705 ± 184 | 4.9 ± 1.3 |
| 23 | III | Methyl | Hydrogen | $CH_2OH$ | 780 ± 280 | | | <10% (10 μM) | 0.8 ± 0.1 |
| 12 | II | 3-iodobenzyl | CONHMe | Hydrogen | 110 ± 12 | 188 ± 40 | 50% (10 μM) | <10% (10 μM) | 4.3 ± 1.2 |
| 33 | III | Methyl | Hydrogen | CONHMe | 1330 ± 242 | 198 ± 14 | 20% (10 μM) | 6340 ± 90 | 0.28 ± 0.09 |
| 36 | III | 3-iodobenzyl | Hydrogen | CONHMe | 193 ± 46 | 140 ± 43 | 223 ± 36 | 348 ± 110 | 0.38 ± 0.07 |
| 29 | III | Hydrogen | Hydrogen | CONHMe | 89.2 ± 11.7 | 294 ± 115 | 158 ± 29 | <10% (10 μM) | 0.40 ± 0.06 |

-continued

| | |
|---|---|
| Lactose | 100 mg |
| Talc | 100 mg |

The ingredients listed above were mixed and loaded into airtight sacks, and powder was prepared.

Formulation Example 2

Tablet Formulation

| | |
|---|---|
| Dry powder of compound 33 | 100 mg |
| Cornstarch | 100 mg |
| Lactose | 100 mg |
| Magnesium stearate | 2 mg |

After the ingredients listed above were mixed together, tablets were made using the conventional tablet manufacturing method.

Formulation Example 3

Capsule Formulation

| | |
|---|---|
| Dry powder of compound 33 | 50 mg |
| Lactose | 50 mg |
| Magnesium stearate | 1 mg |

The ingredients listed above were mixed, then loaded into gelatin capsules made by conventional capsule manufacturing method.

Formulation Example 4

Injection Formulation

| | |
|---|---|
| Dry powder of compound 33 | 10 mg |
| Sterilized distilled water for injection | Appropriate amount |
| pH adjusting agent | Appropriate amount |

According to the manufacturing method for conventional injectable solutions, the active ingredient was dissolved in distilled water for injection and the pH of the solution was adjusted to approximately 7.5. The entire solution was loaded into a 2-mL capacity ampule using distilled water for injection, which was then sterilized to prepare the injectable solution.

Formulation Example 5

Liquid Formulation

| | |
|---|---|
| Dry powder of compound 33 | 1 g |
| Isomerized [sic] saccharide | 10 g |

-continued

| | |
|---|---|
| Saccharide | 10 g |
| Lemon flavor | Appropriate amount |
| Purified water | Appropriate amount |

According to conventional manufacturing methods for liquid drugs, each ingredient was added to purified water and dissolved. After an appropriate amount of the lemon flavor was added and the entire solution was brought to 100 mL by adding the purified water, it was then loaded in a brown bottle and sterilized to prepare a liquid drug.

The aforementioned composition ratio is presented as a preferred example wherein ingredients suitable for beverages are mixed. However, the composition ratio may be altered according to the preferred regional and ethnic taste depending on consumer class, consumer country, application, etc.

Effect of the Invention

New thionucleoside derivative compounds of the present invention and pharmaceutical compositions containing these compounds have selectivity for adenosine $A_3$ receptors, and therefore they can be used as effective drugs for preventing and treating various cancers and inflammatory intestinal diseases and inflammatory diseases.

Example 2

This Example further illustrates a method of making compounds of the present invention.

General. Melting points are uncorrected. 1H NMR (400 MHz), 13C NMR (100 MHz) and $^9$F NMR (376 MHz) spectra were measured in $CDCl_3$ and $CD_3OD$ and chemical shifts are reported in parts per million (δ) downfield from tetramethylsilane as internal standard. Elemental analyses were performed at the general instrument laboratory of Ewha Womans University, Korea. TLC was performed on Merck precoated $60F_{254}$ plates. Column chromatography was performed using silica gel 60 (230–400 mesh, Merck). Anhydrous solvents were purified by the standard procedures.

Figure 2:
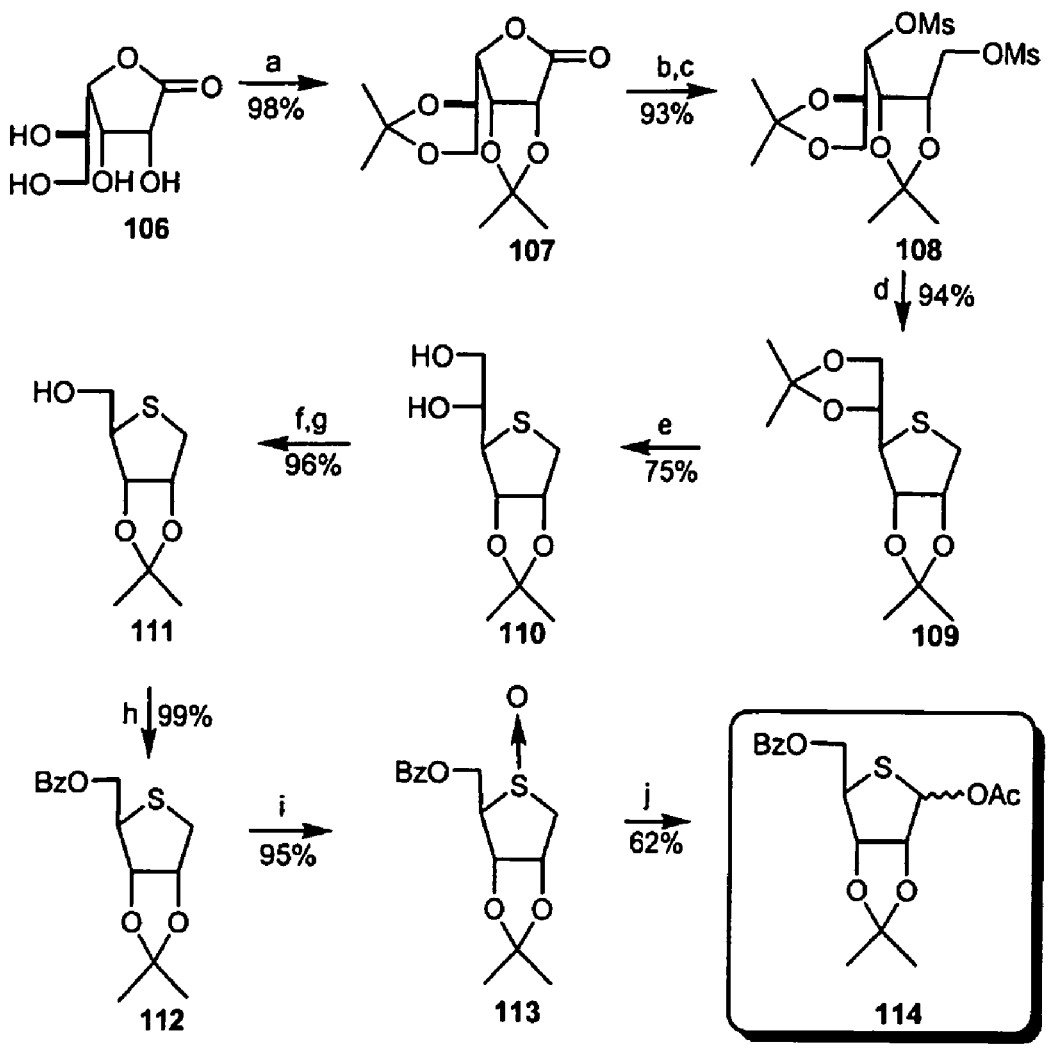
FIG. 2 depicts part of reaction scheme to make compounds in accordance with an embodiment of the present invention.
Figure 3:
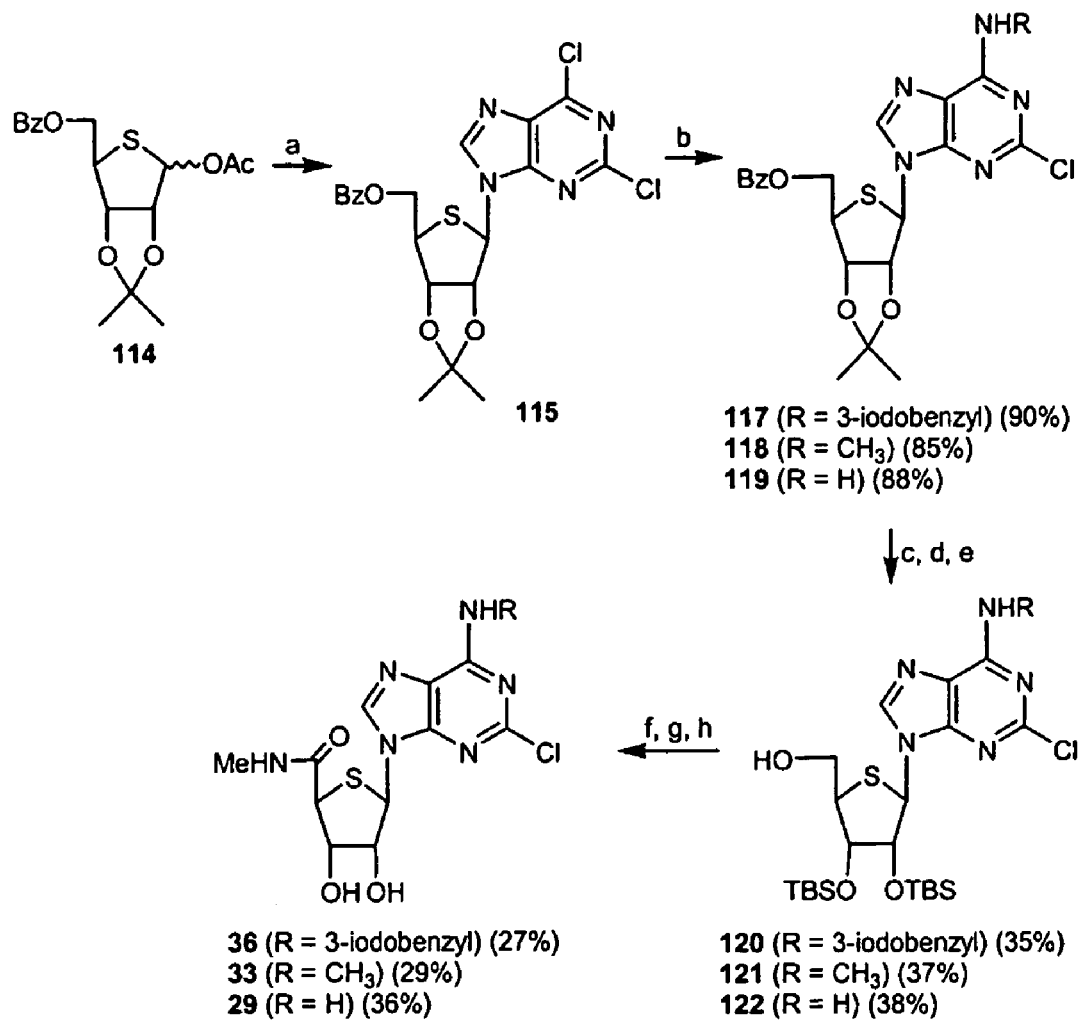
FIG. 3 depicts another part of a reaction scheme to make compounds in accordance with a embodiment of the present invention.

Methanesulfonic acid (S)-((4R)-2,2-dimethyl-[1,3]dioxolan-4-yl)((4S,5S)-5-methanesulfonyloxymethyl-2,2-dimethyl-[1,3]dioxolan-4-yl)-methyl ester (33). Reference is made to FIGS. 1–3.

To a stirred slurry of D-gulonic-γ-lactone 106 (20.2 g, 113.5 mmol) and anhydrous $CuSO_4$ (27.0 g, 169.8 mmol) in dry acetone (650 mL) was added conc. $H_2SO_4$ (1.7 mL), and the mixture was stirred for 24 h at room temperature. The pH of the solution was adjusted to 7 with $Ca(OH)_2$, and the resulting slurry was filtered and evaporated in vacuo to afford the diacetonide 107 (28.7 g, 98%) as a light-yellow syrup. It was used in the next step without further purification. To a stirred solution of diacetonide 107 (25.1 g, 97.2 mmol) in ether (450 mL) was added, cautiously in several portions, lithium aluminum hydride (7.2 g, 190.4 mmol) at 0° C., and the reaction mixture was stirred at room temperature for 10 h. After cooling, the reaction mixture was sequentially treated with water (7.2 mL), 15% aqueous sodium hydroxide solution (7.2 mL), water (21.6 mL), and $MgSO_4$ (19 g), filtered and evaporated under reduced pressure. The resulting residue was purified by silica gel column chromatography (hexane/ethyl acetate=1:1) to give the diol (24.1 g, 95%) as a syrup: $^1$H NMR ($CDCl_3$) δ 1.29 (s, 3H, $CH_3$),1.29 (s, 3H, $CH_3$), 1.36 (s, 3H, $CH_3$),1.43 (s, 3H, $CH_3$),3.26 (s, 1H, OH), 3.28 (s, 1H, OH), 3.36–3.79 (m, 4H, HOCH$_2$, OCH$_2$), 3.96–4.03 (m, 2H, HOCH$_2$CH(OR)R', OCHRR'), 4.12–4.22 (m, 2H); Anal. Calcd for C$_{12}$H$_{22}$O$_6$: C, 54.95; H, 8.45. Found: C, 54.67; H, 8.4.

To a stirred solution of diol (4.1 g, 15.7 mmol) in a mixture of dichloromethane (1000 mL) and pyridine (25 mL) was added methanesulfonyl chloride (18.2 mL, 235.5 mmol) at 0° C. After being stirred at 5° C. for 5 h, the mixture was partitioned between chloroform and saturated aqueous NaHCO$_3$ solution. The aqueous layer was extracted with chloroform and the combined organic extracts were dried, filtered and evaporated. The residue was purified by silica gel column chromatography (hexane/ethyl acetate=2:1) to give the dimesylate 108 (6.4 g, 98%) as a syrup: $^1$H NMR (CDCl$_3$) δ 1.37 (s, 3H, CH$_3$), 1.39 (s, 3H, CH$_3$), 1.46 (s, 3H, CH$_3$), 1.52 (s, 3H, CH$_3$) 3.10 (s, 3H, SO$_2$CH$_3$), 3.18 (s, 3H, SO$_2$CH$_3$), 3.92–4.08 (dd, 1H, J=11.7, 7.1 Hz, ROCHH), 4.08–4.20 (m, 2H, ROCHHCH(OR')), 4.39–4.49 (m, 4H, MsOCH$_2$CH(OR)CH(OR')), 4.81–4.87 (dd, 1H, J=6.6, 4.8 Hz, MsOCHRR'); Anal. Calcd for C$_{14}$H$_{26}$O$_{10}$S$_2$: C, 40.18; H, 6.26, S,15.32. Found: C, 40.32; H, 6.11; S, 15.67.

(3aS,4R,6aR)-4-((4R)-2,2-Dimethyl-[1,3]dioxolan-4-yl)-2,2-dimethyl-tetrahydro-thieno[3,4-d][1,3]dioxole (109)

To a stirred solution of dimesylate 108 (10.1 g, 24.2 mmol) in DMF (260 mL) was added sodium sulfide (8.9 g, 36.3 mmol) and the mixture was heated at 100° C. for 3 h. After the solvent was removed under reduced pressure, the residue was partitioned between ethyl acetate and H$_2$O. The organic layer was washed with brine and water, dried (MgSO$_4$), filtered, and evaporated. The resulting residue was purified by silica gel column chromatography (hexane/ethyl acetate=5:1) to give 109 (5.9 g, 94%) as a syrup: $^1$H NMR (CDCl$_3$) δ 1.33 (s, 3H, CH$_3$), 1.34 (s, 3H, CH$_3$), 1.44 (s, 3H, CH$_3$), 1.52 (s, 3H, CH$_3$), 2.88 (d, 1H, J=12.7 Hz, 6–CHH), 3.09 (td, 1H, J=13.1, 2.2 Hz, 6–CHH), 3.24 (d, 1H, J=8.8 Hz, 4-H), 3.76 (dd, 1H, J=8.6, 5.7 Hz, 5'-CHH), 3.98 (td, 1H, J=9.0, 6.0 Hz, 4'-H). 4.15 (dd, 1H, J=8.5, 6.3 Hz, 5'-CHR), 4.93 (d, 2H, J=1.9 Hz, 3a-H, 6a-H); $^{13}$C NMR (CDCl$_3$) δ 23.8 (CH$_3$), 24.6 (CH$_3$), 25.6 (CH$_3$), 26.1 (CH$_3$), 36.9 (CH$_2$), 56.5 (CH), 68.3 (CH$_2$), 75.6 (CH), 82.3 (CH), 84.5 (CH); FAB-MS m/z 260 (M$^+$); Anal. Calcd for C$_{12}$H$_{20}$O$_4$S: C, 55.36; H, 7.74; S, 12.32. Found: C, 55.24; H, 7.72; S, 12.14.

(1R)-1-((3aS,4R,6aR)-2,2-Dimethyl-tetrahydro-thieno[3,4-d][1,3]dioxol-4-yl)-ethane-1,2-diol (110)

A solution of 109 (5.4 g, 20.1 mmol) in 30% aqueous AcOH (150 mL) was stirred at room temperature for 50 h. The reaction mixture was evaporated under reduced pressure, and the resulting residue was purified by silica gel column chromatography (hexane/ethyl acetate=1:1) to give the diol 110 (3.4 g, 75%) as a syrup: $^1$H NMR (CDCl$_3$) δ 1.34 (s, 3H, CH$_3$), 1.53 (s, 3H, CH$_3$), 2.90 (dd, 1H, J=12.9, 2.2 Hz, 6'-CHH), 3.09 (dd, 1H, J=12.9, 4.8 Hz, 6'-CHH), 3.27 (dd, 1H, J=7.8, 1.9 Hz, 4'-H), 3.49 (br s, 2H, 2×OH), 3.58–3.72 (m, 2H, HOCHHCH(OH)), 3.79 (dd, 1H, J=11.0, 2.9 Hz, HOCHH), 4.93 (m, 2H, 3a-H, 6a-H); Anal. Calcd for C$_{19}$H$_{16}$O$_4$S: C, 49.07; H, 7.32; S, 14.56. Found: C, 49.24; H, 7.72; S, 14.23.

(3aS,4S,6aR)-2,2-Dimethyl-tetrahydro-thieno[3,4-d][1,3]dioxole-4–Carbaldehyde (111).

To a stirred solution of diol 110 (2.5 g, 11.2 mmol) in ethyl acetate (50 mL) was added Pb(OAc)$_4$ (5.4 g, 12.3 mmol) at 0° C. and the reaction mixture was stirred for 10 min at which time TLC indicated the absence of starting material. The reaction mixture was filtered and the filtrate was diluted with EtOAc. The organic layer was washed with saturated aqueous NaHCO$_3$ solution, dried (MgSO$_4$), and evaporated. The residue was purified by silica gel column chromatography (hexane/ethyl acetate=5:1) to give aldehyde 7 (2.1 g, 98%) as a syrup.

$^1$H NMR (CDCl$_3$) δ 1.33 (s, 3H, CH$_3$), 1.52 (s, 3H, CH$_3$), 2.61 (dd, 1H, J=13.2, 3.9 Hz, 6–CHH), 2.87 (dd, 1H, J=12.7, 4.1 Hz, 6–CHH), 3.93 (s, 1H, 4-H), 4.92 (t, 1H, J=4.1 Hz, 6a-H), 5.10 (d, 1H, J=5.4 Hz, 3a-H), 9.43 (s, 1H, CHO).

To a stirred solution of aldehyde (5.6 g, 30.0 mmol) in MeOH (70 mL) was added, cautiously in several portions, sodium borohydride (1.3 g, 33.6 mmol) at 0° C. The reaction mixture was stirred for 30 min at the same temperature, before neutralized with glacial AcOH. After evaporation of most of the solvent, the mixture was partitioned between EtOAc (150 mL) and brine (100 mL). The organic layer was dried, filtered, and evaporated. The resulting residue was purified by silica gel column chromatography (hexane/ethyl acetate=2:1) to give 111 (5.5 g, 98%) as a syrup: $^1$H NMR (CDCl$_3$) δ 1.33 (s, 3H, CH$_3$), 1.53 (s, 3H, CH$_3$), 2.41 (br s, 1H, OH), 2.89 (dd, 1H, J=12.9, 1.5 Hz, 6-CHH), 3.09 (dd, 1H, J=12.7, 4.9 Hz, 6–CHH), 3.44 (td, 1H, J=6.6, 1.0 Hz, 4-H), 3.59 (d, 2H, J=5.4 Hz, HOCH$_2$), 4.71 (dd, 1H, J=5.6, 1.2 Hz, 6a-H), 4.91 (td, 1H, J=5.3, 1.5 Hz, 3a-H); FAB-MS m/z 190 (M$^+$); Anal. Calcd for C$_9$H$_{14}$O$_3$S: C, 50.50; H, 7.42; S, 16.85. Found: C, 50.89; H, 7.72; S, 16.49.

Benzoic acid (3aS,4R,6aR)-2,2-dimethyl-tetrahydro-thieno[3,4-d][1,3]dioxol-4-ylmethyl ester (112)

To a solution of 111 (2.1 g, 11.1 mmol) in pyridine (20 mL) was added benzoyl chloride (1.9 g, 13.4 mmol) at 0° C. and the reaction mixture was stirred for 6 h at room temperature before being quenched with methanol. The reaction mixture was evaporated under reduced pressure. The residue was then taken up in diethyl ether (50 mL), and the pyridinium salt was filtered and washed with diethyl ether. The combined organic layer was concentrated and the resulting residue was purified by silica gel column chromatography (hexane/ethyl acetate=4:1) to afford the benzoate 112 (3.2 g, 99%) as a colorless oil: $^1$H NMR (CDCl$_3$) δ 1.26 (s, 3H, CH$_3$), 1.47 (s, 3H, CH$_3$), 2.87 (dd, 1H, J=13.2, 1.5 Hz, 6-CHH), 3.11 (dd, 1H, J=13.2, 4.9 Hz, 6–CHH), 3.57 (m, 1H, 4-H), 4.25 (dd, 1H, J=11.5, 8.0 Hz, BzOCHH), 4.35 (dd, 1H, J=11.4, 5.8 Hz, BzOCHH), 4.72 (dd, 1H, J=5.6, 1.2 Hz, 6a-H), 4.91 (td, 1H, J=4.4, 1.2 Hz, 3a-H), 7.35–7.99 (m, 5H, Ph); FAB-MS m/z 294 (M$^+$); Anal. Calcd for C$_{15}$H$_{18}$O$_4$S: C, 61.20; H, 6.16; S, 10.89. Found: C, 60.99; H, 6.42; S, 10.77.

Benzoic acid (3aS,4R,6R,6aR)- and (3aS,4R,6S,6aR)-6-acetoxy-2,2-dimethyl-tetrahydro-thieno[3,4-d][1,3]dioxol-4-ylmethyl ester (114)

To a stirred solution of 112 (1.4 g, 4.6 mmol) in CH$_2$Cl$_2$ (30 mL) was added dropwise a solution of m-CPBA (1.0 g, 4.6 mmol, 80%) in CH$_2$Cl$_2$ (15 mL) at −78° C. After being stirred at the same temperature for 45 min, the reaction mixture was quenched by the addition of aqueous saturated NaHCO$_3$ solution. The whole was extracted with CH$_2$Cl$_2$, and the organic layer was washed with brine, dried (MgSO$_4$), filtered, and evaporated. The residue was purified by silica gel column chromatography (hexane/ethyl acetate=2:1) to give the sulfoxide 113 (1.4 g, 95%) as a white solid: $^1$H NMR (CDCl$_3$) of one isomer δ 1.33 (s, 3H, CH$_3$), 1.49 (s, 3H, CH$_3$), 3.23 (dd, 1H, J=14.4, 4.1 Hz, 6–CHH), 3.38 (dd, 1H, J=14.4, 6.3 Hz, 6–CHH), 3.47 (m, 1H, 4-H), 4.73 (dd, 1H, J=11.9, 9.0 Hz, BzOCHH), 4.89 (dd, 1H, J=11.9, 4.9 Hz, BzOCHH), 5.02 (t, 1H, J=6.1 Hz, 3a-H), 5.24 (m, 1H, 6a-H), 7.41–8.03 (m, 5H, Ph).

A solution of sulfoxide 113 (3.5 g, 11.3 mmol) in Ac$_2$O (90 mL) was heated at 100° C. for 6 h. After concentration under reduced pressure, the residue was partitioned between ethyl acetate and H$_2$O. The organic layer was washed with saturated aqueous NaHCO$_3$ solution and brine, dried (MgSO$_4$), filtered, and evaporated under reduced pressure. The residue was purified by silica gel column chromatography (hexane/ethyl acetate=3:1) to give acetate 114 (2.5 g, 62%) as a syrup: $^1$H NMR (CDCl$_3$) of one isomer δ 1.30 (s, 3H, CH$_3$), 1.50 (s, 3H, CH$_3$), 2.03 (s, 3H, COCH$_3$), 3.77 (dd, 1H, J=9.5, 5.8 Hz, 4-H), 4.37 (dd, 1H, J=11.4, 9.8 Hz, BzOCHH), 4.23 (dd, 1H, J=11.4, 6.1 Hz, BzOCHH), 4.94 (d, 1H, J=5.6 Hz, 3a-H), 4.98 (d, 1H, J=5.6 Hz, 6a-H), 6.06 (s, 1H, 6-H), 7.42–8.06 (m, 5H, Ph); FAB-MS m/z 293 (M$^+$-OAc); Anal. Calcd for C$_{17}$H$_{20}$O$_6$S: C, 57.94; H, 5.72; S, 9.10. Found: C, 58.14; H, 5.41; S, 9.34.

Benzoic acid (3aS,4R,6R,6aR)-6-(2,6-dichloro-purin-9-yl)-2,2-dimethyl-tetrahydro-thieno[3,4-d][1,3]dioxol-4-ylmethyl ester (115) and its α-isomer A suspension of 2,6-dichloropurine (415 mg, 2.20 mmol), ammonium sulfate (catalytic amount), and HMDS (80 mL) was refluxed for 6 h under nitrogen to provide the silylated derivative. This clear reaction mixture was concentrated to dryness in vacuo with keeping exclusion of moisture, and the residue was dissolved in dry 1,2-dichloroethane (15 mL). A solution of acetate 114 (668 mg, 1.90 mmol) in dry 1,2-dichloroethane (20 mL) and TMSOTf (0.42 mL, 2.18 mmol) were added at 0° C., and the reaction mixture was stirred for 20 min at the same temperature and then refluxed for 4 h, during which time the initially formed N-3 isomer was converted to N-9 isomer. After saturated aqueous NaHCO$_3$ solution (20 mL) was added, the mixture was stirred for 15 min. Two layers were separated, and the aqueous layer was extracted with methylene chloride. The combining organic layer was washed with brine, dried (MgSO$_4$), filtered, and concentrated under reduced pressure. The residue was purified by silica gel column chromatography (hexane/ethyl acetate=2:1) to give β-anomer 115 (409 mg, 44%) as a white foam and its α-anomer (102 mg, 11%) as a white foam.

β-anomer 115: UV (MeOH) λ$_{max}$ 269 nm (pH 7); $^1$H NMR (CDCl$_3$) δ 1.39 (s, 3H, CH$_3$), 1.64 (s, 3H, CH$_3$), 4.11 (td, 1H, J=6.8, 2.7 Hz, 4-H), 4.57 (dd, 1H, J=11.4, 6.6 Hz, BzOCHH), 4.75 (dd, 1H, J=11.4, 7.1 Hz, BzOCHH), 5.19 (dd, 1H, J=5.4, 2.7 Hz, 3a-H), 5.40 (dd, 1H, J=5.4, 1.9 Hz, 6a-H), 6.10 (d, 1H, J=1.9 Hz, 6-H), 7.37–7.97 (m, 5H, Ph), 8.38 (s, 1H, H-8); FAB-MS m/z 482 (M$^+$+1); Anal. Calcd for C$_{20}$H$_{18}$Cl$_2$N$_4$O$_4$S: C, 49.90; H, 3.77; N, 11.64; S, 6.66. Found: C, 49.53; H, 3.42; N, 11.93; S, 6.36.

α-anomer: UV (MeOH) λ$_{max}$ 279 nm (pH 7); $^1$H NMR (CDCl$_3$) δ 1.37 (s, 3H, CH$_3$),1.64 (s, 3H, CH$_3$), 4.08 (m, 1H, 4-H), 4.51 (dd, 1H, J=11.7, 6.3 Hz, BzOCHH), 4.62 (dd, 1H, J=11.7, 7.1 Hz, BzOCHH), 5.01 (m, 1H, 3a-H), 5.11 (m, 1H, 6a-H), 6.50 (d, 1H, J=2.2 Hz, 6-H), 7.37–7.99 (m, 5H, Ph), 8.87 (s, 1H, H-8); FAB-MS m/z 482 (M$^+$+1); Anal. Calcd for C$_{20}$H$_{18}$Cl$_2$N$_4$O$_4$S: C, 49.90; H, 3.77; N, 11.64; S, 6.66. Found: C, 49.57; H, 4.01; N, 11.92; S, 6.58.

Benzoic acid (3aS,4R,6R,6aR)-6-[2-chloro-6-(3-iodo-benzylamino)purin-9-yl]-2,2-dimethyl-tetrahydro-thieno[3,4-d][1,3]dioxol-4-ylmethyl ester (117)

A solution of 115 (254 mg, 0.53 mmol), 3-iodobenzylamine hydrochloride (200 mg, 0.68 mmol), and triethylamine (0.22 mL, 1.53 mmol) in ethanol (1.5 mL) was stirred at room temperature for 3 d. The reaction mixture was evaporated under reduced pressure, and the resulting residue was purified by silica gel column chromatography (hexane/ethyl acetate=1:1) to give 117 (322 mg, 90%) as a white foam: UV (MeOH) λmax 272 nm (pH 7); $^1$H NMR (CDCl$_3$) δ 1.37 (s, 3H, CH$_3$), 1.63 (s, 3H, CH$_3$), 4.11 (td, 1H, J=7.3, 2.7 Hz, 4-H), 4.57 (dd, 1H, J=11.4, 6.8 Hz, BzOCHH), 4.76 (m, 3H, BzOCHH, N—CH$_2$), 5.22 (dd, 1H, J=5.6, 2.7 Hz, 3a-H), 5.38 (dd, 1H, J=5.6, 1.9 Hz, 6a-H), 6.01 (d, 1H, J=1.9 Hz, 6-H), 6.28 (br s, 1H, NH), 7.04–8.02 (m, 10H, aromatic H); FAB-MS m/z 679 (M$^+$+1);

Anal. Calcd for C$_{27}$H$_{25}$ClIN$_5$O$_4$S: C, 47.83; H, 3.72; N, 10.33; S, 4.73. Found: C, 47.50; H, 3.48; N, 10.69; S, 4.48.

Benzoic acid (3aS,4R,6R,6aR)-6-(2-chloro-6-methylamino-purin-9-yl)-2,2-dimethyl-tetrahydro-thieno[3,4-d][1,3]dioxol-4-ylmethyl ester (118)

A solution of 115 (454 mg, 0.94 mmol) in CH$_3$NH$_2$ (20 mL, 40 mmol, 2 N THF solution) was stirred at room temperature in a sealed tube for 24 h. After the reaction mixture was concentrated to dryness, the residue was purified by silica gel column chromatography (hexane/ethyl acetate=1:1) to give 118 (383 mg, 85%) as a white foam: UV (MeOH) λ$_{max}$ 271 nm (pH 7); $^1$H NMR (CDCl$_3$) δ 1.37 (s, 3H, CH$_3$), 1.63 (s, 3H, CH$_3$), 3.02 (d, 3H, J=4.9 Hz, N—CH$_3$), 4.01 (td, 1H, J=7.8, 2.7 Hz, 4-H), 4.57 (dd, 1H, J=11.5, 6.8 Hz, BzOCHH), 4.75 (dd, 1H, J=11.5, 7.8 Hz, BzOCHH), 5.23 (dd, 1H, J=5.6, 2.9 Hz, 3a-H), 5.38 (dd, 1H, J=5.6, 1.9 Hz, 6a-H), 6.01 (d, 1H, J=1.9 Hz, 6-H), 6.16 (br s, 1H, NH), 7.40–8.02 (m, 6H, Ph, H-8); FAB-MS m/z 477 (M$^+$+1); Anal. Calcd for C$_{21}$H$_{22}$ClN$_5$O$_4$S: C, 52.99; H, 4.66; N, 14.71; S, 6.74. Found: C, 52.71; H, 4.49; N, 14.76; S, 6.64.

Benzoic acid (3aS,4R,6R,6aR)-6-(6-amino-2-chloro-purin-9-yl)-2,2-dimethyl-tetrahydro-thieno[3,4-d][1,3]dioxol-4-yl methyl ester (19)

A solution of 115 (454 mg, 0.94 mmol) in saturated ethanolic ammonia (25 mL) was heated at 50° C. in a sealed tube for 24 h. The reaction mixture was evaporated to dryness under reduced pressure. The resulting residue was purified by silica gel column chromatography (hexane/ethyl acetate=1:1) to afford 119 (384 mg, 88%) as a white foam: UV (MeOH) λ$_{max}$ 264 nm (pH 7); $^1$H NMR (CDCl$_3$) δ 1.37 (s, 3H, CH$_3$), 1.63 (s, 3H, CH$_3$), 4.01 (td, 1H, J=7.3, 2.7 Hz, 4-H), 4.57 (dd, 1H, J=11.5, 6.8 Hz, BzOCHH), 4.77 (dd, 1H, J=11.5, 7.6 Hz, BzOCHH), 5.23 (dd, 1H, J=5.6, 2.7 Hz, 3a-H), 5.38 (dd, 1H, J=5.6, 1.9 Hz, 6a-H), 6.02 (d, 1H, J=1.9 Hz, 6-H), 6.29 (br s, 2H, NH$_2$), 7.40–8.02 (m, 6 H, Ph, H-8); FAB-MS m/z 463 (M$^+$+1); Anal. Calcd for C$_{20}$H$_{20}$ClN$_5$O$_4$S: C, 52.00; H, 4.36; N, 15.16; S, 6.94. Found: C, 52.32; H, 4.42; N, 14.89; S, 6.71.

{(2R,3S,4R,5R)-3,4-Bis-(tert-butyl-dimethyl-silanyloxy)-5-[2-chloro-6-(3-iodo-benzylamino)purin-9-yl]-tetrahydro-thiophen-2-yl}-methanol (120)

A solution of 117 (122 mg, 0.18 mmol) in 80% aqueous AcOH solution (6 mL) was stirred at 55° C. for 12 h. The solvent was removed under reduced pressure. After neutralized with methanolic ammonia, the residue was purified by silica gel column chromatography ($CH_2Cl_2$/MeOH=15:1) to give diol (73 mg, 64%) as a white foam. To a stirred solution of diol (450 mg, 0.71 mmol) and imidazole (286 mg, 4.20 mmol) in dry DMF (15 mL) was added dropwise a solution of tert-butylchlorodimethylsilane (316 mg, 2.10 mmol) in dry DMF (5 mL) and the reaction mixture was stirred at 50° C. for 24 h. The mixture was partitioned between $CH_2Cl_2$ and water, and the organic layer was washed with water, aqueous $NaHCO_3$ solution, water, and brine, and dried ($MgSO_4$). Filtration and evaporation of the mixture under reduced pressure gave the crude disilyl ether, which was used in the next step without further purification. To a stirred solution of disilyl ether in methanol (15 mL) was added sodium methoxide (90 mg, 1.74 mmol) and the mixture was stirred at room temperature for 4 h. After being neutralized with glacial acetic acid, the mixture was evaporated under reduced pressure to give the resulting residue, which was purified by silica gel column chromatography (hexane/ethyl acetate=2:1) to give 120 (290 mg, 54%) as a white solid: UV (MeOH) $\lambda_{max}$ 272 nm (pH 7); $^1$H NMR ($CDCl_3$) δ 0.01 (m, 12H, 4×Si—$CH_3$), 0.80 (s, 9H, $C(CH_3)_3$), 0.85 (s, 9H, $C(CH_3)_3$), 3.29 (dd, 1H, J=11.4, 5.8 Hz, 2-H), 4.24 (m, 1H, HOCHH), 4.47 (dd, 1H, J=11.9, 5.8 Hz, 3-H), 4.73 (m, 3H, HOCHH, N—$CH_2$), 4.86 (dd, 1H, J=11.9, 6.3 Hz, 4-H), 5.67 (d, 1H, J=4.6 Hz, 5-H), 6.15 (br t, 1H, exchangeable with $D_2O$, OH), 7.02 (t, 1H, J=7.7 Hz, 5'-H), 7.27 (d, 1H, J=7.5 Hz, 6'-H), 7.43 (d, 1H, J=7.8 Hz, 4'-H), 7.59 (br s, 1H, exchangeable with $D_2O$, NH), 7.67 (s, 1H, 2'-H), 8.03 (s, 1H, H-8); FAB-MS m/z 763 ($M^+$+1); Anal. Calcd for $C_{29}H_{45}ClIN_5O_3SSi_2$: C, 45.69; H, 5.95; N, 9.19; S, 4.21. Found: C, 45.47; H, 5.92; N, 8.97; S, 4.39.

[(2R,3S,4R,5R)-3,4-Bis-(tert-butyl-dimethyl-silanyloxy)-5-(2-chloro-6-methylamino-purin-9-yl)tetrahydro-thiophen-2-yl]-methanol (121)

Compound 115 (105 mg, 0.22 mmol) was converted to diol (65 mg, 68%) as a white foam. Diol (160 mg, 0.38 mmol) was converted to 121 (112 mg, 54%) as a white solid according to the same procedure used in the synthesis of 120: UV (MeOH) $\lambda_{max}$ 269 nm (pH 7); $^1$H NMR ($CDCl_3$) δ 0.01 (m, 12H, 4×Si—$CH_3$), 0.81 (s, 9H, $C(CH_3)_3$), 0.86 (s, 9H, $C(CH_3)_3$), 3.13 (br s, 3H, N—$CH_3$), 3.72 (dd, 1H, J=11.7, 5.8 Hz, 2-H), 4.24 (m, 1H, 3-H), 4.48 (dd, 1H, J=11.7, 5.8 Hz, HOCHH), 4.75 (m, 1H, 4-H), 4.87 (dd, 1H, J=11.7, 6.3 Hz, HOCHH), 5.67 (d, 1H, J=4.6 Hz, 5-H), 5.88 (br s, 1H, exchangeable with $D_2O$, OH), 8.00 (s, 1H, H-8), 8.03 (br s, 1H, exchangeable with $D_2O$, NH).

[(2R,3S,4R,5R)-5-(6-Amino-2-chloro-purin-9-yl)-3,4-bis-(tert-butyl-dimethyl-silanyloxy)-tetrahydro-thiophen-2-yl]-methanol (122)

Compound 115 (102 mg, 0.22 mmol) was converted to diol (63 mg, 68%) as a white foam. Diol (230 mg, 0.55 mmol) was converted to 122 (169 mg, 56%) as a white solid according to the same procedure used in the synthesis of 120: UV (MeOH) $\lambda_{max}$ 263 nm (pH 7); $^1$H NMR ($CDCl_3$) δ 0.01 (m, 12H, 4×Si—$CH_3$), 0.79 (s, 9H, $C(CH_3)_3$), 0.83 (s, 9H, $C(CH_3)_3$), 3.41 (dd, 1H, J=11.2, 4.7 Hz, 2-H), 4.21 (m, 1H, HOCHH), 4.56 (dd, 1H, J=10.9, 4.7 Hz, 3-H), 4.73 (m, 1H, HOCHH), 4.86 (dd, 1H, J=10.9, 5.8 Hz, 4-H), 5.71 (d, 1H, J=5.8 Hz, 5-H), 6.20 (br d, 1H, exchangeable with $D_2O$, OH), 7.61 (br s, 2H, exchangeable with $D_2O$, $NH_2$), 8.12 (s, 1H, H-8).

(2S,3S,4R,5R)-5-[2-chloro-6-(3-iodo-benzylamino)-purin-9-yl]-3,4-dihydroxy-tetrahydro-thiophene-2-carboxylic acid methylamide (36)

To a stirred solution of 120 (228 mg, 0.30 mmol) in dry DMF (20 mL) was added pyridinium dichromate (2.6 g, 6.91 mmol) and the reaction mixture was stirred at room temperature for 20 h. After being poured into water (30 mL), the reaction mixture was extracted with EtOAc (100 mL×5). The organic layer was dried ($MgSO_4$), and evaporated to give the crude carboxylic acid, which was dried for 2 d under vacuum and used in the next reaction without further purification. A suspension of the crude carboxylic acid, dimethyl sulfate (1 mL, 10.57 mmol) and $K_2CO_3$ (100 mg, 0.72 mmol) in acetone (6 mL) was stirred at room temperature for 2 h. After the reaction mixture was evaporated, the residue was dissolved in ethyl acetate, washed with water and brine, dried ($MgSO_4$), and evaporated to give methyl ester (200 mg), which was used in the next step without further purification. A stirred solution of crude methyl ester (200 mg) in methylamine (20 mL, 40.0 mmol, 2 N THF solution) was heated at 50° C. for 24 h in a sealed tube. The volatiles were removed under reduced pressure, and the resulting residue was purified by silica gel column chromatography (hexane/ethyl acetate=1:2) to give silyl amide (99 mg, 42%) as a white foam: UV (MeOH) $\lambda_{max}$ 272 nm (pH 7); $^1$H NMR ($CDCl_3$) δ 0.01 (m, 12H, 4×Si—$CH_3$), 0.70 (s, 9H, $C(CH_3)_3$), 0.84 (s, 9H, $C(CH_3)_3$), 2.70 (d, 3H, J=4.7 Hz, N—$CH_3$), 3.81 (d, 1H, J=4.7 Hz, 2-H), 4.39 (m, 1H, 3-H), 4.55 (m, 1H, 4-H), 4.61 (d, 2H, J=5.7 Hz, N—$CH_2$), 5.83 (d, 1H, J=5.4 Hz, 5-H), 7.15 (t, 1H, J=7.7 Hz, 5'-H), 7.36 (d, 1H, J=7.5 Hz, 6'-H), 7.61 (d, 1H, J=7.8 Hz, 4'-H), 7.76 (s, 1H, 2'-H), 8.33 (br s, 1H, exchangeable with $D_2O$, NH), 8.61 (s, 1H, H-8), 9.00 (br s, 1H, exchangeable with $D_2O$, NH); FAB-MS m/z 790 ($M^+$+1); Anal. Calcd for $C_{30}H_{46}ClIN_6O_3SSi_2$: C, 45.65; H, 5.87; N, 10.65; S, 4.06. Found: C, 45.34; H, 5.55; N, 10.37; S, 4.34.

To a stirred solution of silyl amide (75 mg, 0.09 mmol) in THF (5 mL) was added TBAF (0.25 mL, 0.25 mmol, 1M THF solution) and the reaction mixture was stirred at room temperature for 1 h. The solvent was evaporated and the resulting residue was purified by silica gel column chromatography ($CH_2Cl_2$/MeOH=7:1) to give 36 (33 mg, 63%) as a white solid: mp 140–141° C.; $[α]^{25}_D$ −19.5° (c 0.32, MeOH); UV (MeOH) $\lambda_{max}$ 272 nm (pH 7); $^1$H NMR (DMSO-$d_6$) δ 2.69 (d, 3H, J=4.5 Hz, N—$CH_3$), 3.82 (d, 1H, J=4.6 Hz, 2H), 4.37 (br dd, 1H, J=8.4, 4.6 Hz, 3-H), 4.55 (m, 1H, 4-H), 4.60 (d, 2H, J=5.7 Hz, N—$CH_2$), 5.59 (d, 1H, J=5.5 Hz, exchangeable with $D_2O$, OH), 5.78 (d, 1H, J=5.1 Hz, exchangeable with $D_2O$, OH), 5.83 (d, 1H, J=5.4 Hz, 5-H), 7.13 (t, 1H, J=7.8 Hz, 5'-H), 7.35 (d, 1H, J=7.6 Hz, 6'-H), 7.60 (d, 1H, J=7.8 Hz, 4'-H), 7.75 (s, 1H, 2'-H), 8.32 (br q, 1H, exchangeable with $D_2O$, NH), 8.60 (s, 1H, H-8), 8.99 (br t, 1H, J=6.1 Hz, exchangeable with $D_2O$, NH); $^{13}$C NMR (DMSO-$d_6$) δ 42.5 (CH), 51.8 ($CH_2$), 59.7 (CH), 62.6 (CH), 75.4 ($CH_3$), 78.2 (CH), 118.4 (C), 126.8 (CH), 130.5 (CH), 135.5 (CH), 136.0 (CH), 140.3 (C), 141.8 (C), 149.9 (C), 153.0 (C), 154.7 (CH), 170.3 (C), 170.7 (C); FAB-MS m/z 561 (M⁺); Anal. Calcd for $C_{18}H_{18}ClN_6O_3S$: C, 38.55; H, 3.24; N, 14.99; S, 5.72. Found: C, 38.45; H, 3.40; N, 14.97; S, 5.61.

(2S,3S,4R,5R)-5-(2-chloro-6-methylamino-purin-9-yl 3,4-dihydroxy-tetrahydro-thiophene-2-carboxylic acid methylamide (33)

Compound 21 (105 mg, 0.19 mmol) was converted to the silyl amide (48 mg, 44%) as a white foam according to the same procedure used in the synthesis of 36: UV (MeOH) λ max 270 nm (pH 7); ¹H NMR (CDCl₃) δ 0.01 (m, 12H, 4×Si—CH₃), 0.82 (s, 9H, C(CH₃)₃), 0.85 (s, 9H, C(CH₃)₃), 3.21 (br s, 3H, N—CH₃), 3.21 (br s, 3H, N—CH₃), 3.75 (d, 1H, J=4.8 Hz, 2-H), 4.28 (m, 1H, 3-H), 4.65 (m, 1H, 4-H), 5.77 (d, 1H, J=4.6 Hz, 5-H), 7.12 (br s, 1H, exchangeable with D₂O, NH), 8.03 (br s, 1H, exchangeable with D₂O, NH), 8.44 (s, 1H, H-8).

Silyl amide (48 mg, 0.08 mmol) was converted to compound 33 (19 mg, 65%) as a white solid according to the same procedure used in the synthesis of 36.

Compound 33: mp 139–141° C.; [α]¹⁹_D −22.0° (c 0.13, MeOH); UV (MeOH) λ_max 270 nm (pH 7); ¹H NMR (DMSO-d₆) δ 2.69 (d, 3H, J=4.5 Hz, N—CH₃), 2.92 (d, 3H, J=4.0 Hz, N—CH₃), 3.81 (d, 1H, J=4.6 Hz, 2-H), 4.36 (br dd, 1H, J=8.5, 4.8 Hz, 3-H), 4.52 (br dd, 1H, J=8.5, 5.0 Hz, 4-H), 5.61 (d, 1H, J=5.4 Hz, exchangeable with D₂O, OH), 5.78 (d, 1H, J=5.1 Hz, exchangeable with D₂O, OH), 5.82 (d, 1H, J=5.5 Hz, 5-H), 8.33 (br q, 2H, exchangeable with D₂O, NH, NH), 8.54 (s, 1H, H-8); ¹³C NMR (DMSO-d₆) δ 51.8 (CH₃), 55.5 (CH), 62.6 (CH), 69.6 (CH), 75.4 (CH₃), 78.2 (CH), 118.5 (C), 139.9 (C), 149.5 (C), 153.3 (C), 155.5 (CH), 170.7 (C); FAB-MS m/z 359 (M⁺); Anal. Calcd for $C_{12}H_{15}ClN_6O_3S$: C, 40.17; H, 4.21; N, 23.42; S, 8.94. Found: C, 40.21; H, 4.42; N, 23.57; S, 8.98.

(2S,3S,4R,5R)-5-(6-Amino-2-chloro-purin-9-yl)-3,4-dihydroxy-tetrahydro-thiophene-2-carboxylic acid methylamide (29)

Compound 122 (150 mg, 0.27 mmol) was converted to the silyl amide (80 mg, 51%) as a white foam according to the same procedure used in the synthesis of 36: UV (MeOH) A max 264 nm (pH 7); ¹H NMR (CDCl₃) δ 0.01 (m, 12H, 4×Si—CH₃), 0.79 (s, 9H, C(CH₃)₃), 0.85 (s, 9H, C(CH₃)₃), 2.67 (d, 3H, J=4.1 Hz, N—CH₃), 3.78 (d, 1H, J=4.8 Hz, 2-H), 4.35 (m, 1H, 3-H), 4.57 (m, 1H, 4-H), 5.70 (d, 1H, J=5.6 Hz, 5-H), 7.72 (br s, 2H, exchangeable with D₂O, NH₂), 7.72 (br s, 1H, exchangeable with D₂O, NH), 8.10 (s, 1H, H-8).

Silyl amide (140 mg, 0.24 mmol) was converted to compound 29 (58 mg, 69%) as a white solid according to the same procedure used in the synthesis of 36: mp 233–235° C.; [α]²⁶_D −20.2 (c 0.1, MeOH); UV (MeOH) λ_max 264 nm (pH 7); ¹H NMR (DMSO-d₆) δ 2.70 (d, 3H, J=4.1 Hz, N—CH₃), 3.82 (d, 1H, J=4.6 Hz, 2-H), 4.36 (dd, 1H, J=8.7, 4.6 Hz, 3-H), 4.53 (m, 1H, 4-H), 5.60 (d, 1H, J=5.4 Hz, exchangeable with D₂O, OH), 5.78 (d, 1H, J=5.1 Hz, exchangeable with D₂O, OH), 5.82 (d, 1H, J=5.5 Hz, 5-H), 7.87 (br s, 2H, exchangeable with D₂O, NH₂), 8.33 (br q, 1H, exchangeable with D₂O, NH), 8.55 (s, 1H, H-8); ¹³C NMR (DMSO-d₆) δ 51.8 (CH), 57.5 (CH), 62.5 (CH₃), 75.4 (CH), 78.1 (CH), 118.4 (C), 140.1 (C), 150.5 (C), 153.0 (C), 156.7 (CH), 170.7 (C); FAB-MS m/z 345 (M⁺); Anal. Calcd for $C_{11}H_{13}ClN_6O_3S$: C, 38.32; H, 3.80; N, 24.38; S, 9.30. Found: C, 38.70; H, 3.75; N, 24.57; S, 9.62.

[125I]N⁶-(4-amino-3-iodobenzyl)adenosine-5'-N-methyluronamide (1-AB-MECA; 2000 Ci/mmol), [³H]8-ethyl-4-methyl-2-phenyl-(8R)-4,5,7,8-tetrahydro-1H-imidazo[2,1-i]-purin-5-one (PSB-11, 53 Ci/nmol) and [³H]cyclic AMP (40 Ci/mmol) were from Amersharn Pharmacia Biotech (Buckinghamshire, UK).

Cell Culture and Membrane Preparation

CHO (Chinese hamster ovary) cells expressing recombinant the human A₃AR were cultured in DMEM supplemented with 10% fetal bovine serum, 100 units/mL penicillin, 100 μg/mL streptomycin, 2 μmol/mL glutamine and 800 μg/mL geneticin. The CHO cells expressing rat A₃ARs were cultured in DMEM and F 12 (1:1). Cells were harvested by trypsinization. After homogenization and suspension, cells were centrifuged at 500 g for 10 min, and the pellet was re-suspended in 50 mM Tris HCl buffer (pH 8.0) containing 10 mM MgCl₂, 1 mM EDTA and 0.1 mg/mL CHAPS. The suspension was homogenized with an electric homogenizer for 10 sec, and was then re-centrifuged at 20,000 g for 20 min at 4° C. The resultant pellets were resuspended in buffer in the presence of 3 Units/mL adenosine deaminase, and the suspension was stored at −80° C. until the binding experiments. Striatal and forebrain tissues from Wistar rats were homogenized in ice-cold 50 mM Tris.HCl buffer, pH 7.4, using an electric homogenizer. The homogenate was centrifuged at 20,000 g for 10 min at 4° C., and the pellet was washed in fresh buffer. The final pellet was stored at −80° C. until the binding experiments. The protein concentration was measured using the Bradford assay (Bradford, M. M. A rapid and sensitive method for the quantitation of microgram quantities of protein utilizing the principle of protein-dye binding. *Anal. Biochem.* 1976, 72, 248–254).

Binding Assay Using [¹²⁵I]4-*amino-3-iodobenzyl)adenosine-5'-N-methyluronamide*

For competitive binding assay, each tube contained 50 μL membrane suspension (20 μg protein), 25 μl [¹²⁵I]4-amino-3-iodobenzyl)adenosine-5'-N-methyluronamide (1.0 nM), and 25 μL of increasing concentrations of the test ligands in Tris HCl buffer (50 mM, pH 8.0) containing 10 mM MgCl₂, 1 mM EDTA. Nonspecific binding was determined using 10 μM of 112 in the buffer. The mixtures were incubated at 37° C. for 60 min. Binding reactions were terminated by filtration through Whatman GF/B filters under reduced pressure using a MT-24 cell harvester (Brandell, Gaithersburgh, Md., USA). Filters were washed three times with 9 mL ice-cold buffer. Radioactivity was determined in a Beckman 5500γ-counter.

Cyclic AMP Accumulation Assay

Intracellular cyclic AMP levels were measured with a competitive protein binding method (Nordstedt, C.; Fredholm, B. B. A modification of a protein-binding method for rapid quantification of cAMP in cell-culture supernatants and body fluid. *Anal. Biochem.* 1990, 189, 231–234; Post S. R.; Ostrom R. S.; Insel P. A. Biochemical methods for detection and measurement of cyclic AMP and adenylyl cyclase activity. *Methods Mol. Biol.* 2000, 126, 363–374). CHO cell that expressed recombinant human and rat A₃ARs were harvested by trypsinization. After centrifugation and resupended in medium, cells were planted in 24-well plates in 1.0 mL medium. After 24 h, the medium was removed and cells were washed three times with 1 mL DMEM, containing 50 mM HEPES, pH 7.4. Cells were then treated with agonists and/or test compounds in the presence of rolipram (10 μM) and adenosine deaminase (3 units/mL). After 45 min forskolin (10 μM) was added to the medium, and incubation was continued an additional 15 min. The reaction was terminated by removing the supernatant, and cells were lysed upon the addition of 200 μL of 0.1 M ice-cold HCl. The cell lysate was resuspended and stored at −20° C. For determination of cyclic AMP production, protein kinase A (PKA) was incubated with [$^3$H]cyclic AMP (2 nM) in K$_2$HPO$_4$/EDTA buffer (K$_2$HPO$_4$,150 mM; EDTA, 10 mM), 20 μL of the cell lysate, and 30 μL 0.1 M HCl or 50 μL of cyclic AMP solution (0–16 pmol/200 μL for standard curve). Bound radioactivity was separated by rapid filtration through Whatman GF/C filters and washed once with cold buffer. Bound radioactivity was measured by liquid scintillation spectrometry.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is language (e.g., "such as") provided herein, is intended merely to better illuminate the invention and does not pose a limitation on the scope of the invention unless otherwise claimed. No language in the specification should be construed as indicating any non claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. (2R,3S,4R)-2-[2-chloro-6-(3-iodobenzylamino)purin-9-yl]-3,4-dihydroxytetrahydrothiophene-2-carboxylic acid methyl amide.

2. A compound selected from the group consisting of (2R,3R,4S,5R)-2-[2-chloro-6-(3-iodobenzylamino)purin-9-yl]-5-hydroxymethyltetrahydrothiophene-3,4-diol, (2R,3R,4S,5R)-2-(2-chloro-6-methylaminopurin-9-yl]-5-hydroxymethyl-tetrahydrothiophene-3,4-diol, (2S,3S,4R,5R)-5-(6-amino-2-chloro-purin-9-yl]-3,4-dihydroxytetrahydrothiophene-2-carboxylic acid methyl amide, (2S,3S,4R,5R)-5-(2chloro-6-methylaminopurin-9-yl]-3,4-dihydroxytetrahydrothiophene-2-carboxylic acid methyl amide, and (2S,3S,4R,5R)-5-[2-chloro-6-(3-iodobenzylamino)purin-9-yl]-3,4-dihydroxytetrahydrothiophene-2-carboxylic acid methyl amide.

3. (2S,3R,4S,5R)-2-[2-chloro-6-(3-iodobenzylamino)purin-9-yl]-5-hydroxymethyltetrahydrothiophene-3,4-diol.

4. A pharmaceutical composition comprising a compound of claim 1 and a pharmaceutically acceptable carrier.

5. A pharmaceutical composition comprising a compound of claim 2 and a pharmaceutically acceptable carrier.

6. A pharmaceutical composition comprising a compound of claim 3 and a pharmaceutically acceptable carrier.

7. The compound of claim 2, which is (2S,3S,4R,5R)-5-(6-amino-2-chloro-purin-9-yl]-3,4-dihydroxytetrahydrothiophene-2-carboxylec acid methyl amide.

8. A pharmaceutical composition comprising the compound of claim 7 and a pharmaceutically acceptable carrier.

9. The compound of claim 2, which is (2S,3S,4R,5R)-5-[2-chloro-6-(3-iodobenzylamino)purin-9-yl]-3,4-dihydroxytetrahydrothiophene-2-carboxylic acid methyl amide.

10. A pharmaceutical composition comprising a compound of claim 9 and aphannaceutically acceptable carrier.

11. A method of treating breast cancer in an animal comprising administering to the animal an effective amount of the compound of claim 9.

* * * * *